US011058644B2

(12) United States Patent
Gong et al.

(10) Patent No.: US 11,058,644 B2
(45) Date of Patent: Jul. 13, 2021

(54) UNIMOLECULAR NANOPARTICLES FOR EFFICIENT DELIVERY OF THERAPEUTIC RNA

(71) Applicant: Wisconsin Alumni Research Foundation, Madison, WI (US)

(72) Inventors: Shaoqin Gong, Middleton, WI (US); Guojun Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/819,424

(22) Filed: Nov. 21, 2017

(65) Prior Publication Data

US 2018/0140557 A1    May 24, 2018

Related U.S. Application Data

(60) Provisional application No. 62/426,004, filed on Nov. 23, 2016.

(51) Int. Cl.
| | | |
|---|---|---|
| C12N 15/11 | (2006.01) |
| A61K 9/51 | (2006.01) |
| A61K 31/713 | (2006.01) |
| A61P 35/00 | (2006.01) |

(52) U.S. Cl.
CPC .......... *A61K 9/5146* (2013.01); *A61K 9/5192* (2013.01); *A61K 31/713* (2013.01); *A61P 35/00* (2018.01)

(58) Field of Classification Search
CPC .... A61K 31/713; A61K 38/00; A61K 9/5146; A61K 47/64; A61K 47/645; A61K 2039/645; A61K 6/51; A61K 47/6929; A61K 47/6935; A61P 35/00
See application file for complete search history.

(56) References Cited

U.S. PATENT DOCUMENTS 5,661,025 A * 8/1997 Szoka, Jr. ............ A61K 9/1271
                                                         435/375
2013/0332133 A1   12/2013 Horn et al.

FOREIGN PATENT DOCUMENTS

WO    WO-2015/089419 A2    6/2015

OTHER PUBLICATIONS

Kesharwani et al., PAMAM dendrimers as promising nanocarriers for RNAi therapeutics, Materials Today, vol. 18, pp. 565-572. (Year: 2015).*
Meyer et al., Synthesis and biological evaluation of a bioresponsive and endosomolytic siRNA-polymer conjugate, Molecular Pharmaceutics, vol. 6, pp. 752-762. (Year: 2009).*
Guidry et al., Improving the in vivo therapeutic index of siRNA polymer conjugates through increasing pH responsiveness, Bioconjugate Chemistry, vol. 25, pp. 296-307. (Year: 2014).*
Han et al., Transfection study using multicellular tumor spheroids for screening non-viral polymeric gene vectors with low cytotoxicity and high transfection efficiencies, Journal of Controlled Release, vol. 121, pp. 38-48. (Year: 2007).*
Yu et al., Polyactide-graft-doxorubicin nanoparticles with precisely controlled drug loading for pH-triggered drug delivery, Biomacromolecules, vol. 15, pp. 524-532. (Year: 2014).*
Möller et al., Highly efficient siRNA delivery from core-shell mesoporous silica nanoparticles with multifunctional polymer caps, Nanoscale, vol. 8, pp. 4007-4019. (Year: 2016).*
Byrom, et al., "Inducing RNAi with siRNA Cocktails Generated by RNase III," AmbionTechNotes, 2003, pp. 4-6, vol. 10, No. 1.
Calegari, et al., "Tissue-specific RNA interference in postimplantation mouse embryos with endoribonuclease-prepared short interfering RNA," PNAS, Oct. 29, 2002, pp. 14236-14240, vol. 99, No. 22.
Kawasaki, et al., "siRNAs generated by recombinant human Dicer induce specific and significant but target site-independent gene silencing in human cells," Nucleic Acids Research, Feb. 1, 2003, pp. 981-987, vol. 31, Issue 3.
Knight, et al., "A Role for the RNase III Enzyme DCR-1 in RNA Interference and Germ Line Development in Caenorhabditis elegans," Science, Sep. 21, 2001, pp. 2269-2271, vol. 293, Issue 5538.
Prabaharan, et al., "Amphiphilic Multi-Arm-Block Copolymer Conjugated with Doxorubicin Via pH-Sensitive Hydrazone Bond for Tumor-Targeted Drug Delivery," Biomaterials, Oct. 2009, pp. 5757-5766, vol. 30, Issue 29.
Robertson, et al., "Purification and Properties of Ribonuclease III from *Escherichia coli*," Journal of Biological Chemistry, Jan. 10, 1968, pp. 82-91, vol. 243, No. 1.
Segovia, et al., "Hydrogel doped with nanoparticles for local sustained release of siRNA in breast cancer," Advanced Healthcare Materials, Jan. 28, 2015, pp. 271-280, vol. 4, Issue 2.
Yang, et al., "Short RNA duplexes produced by hydrolysis with *Escherichia coli* RNase III mediate effective RNA interference in mammalian cells," PNAS, Jul. 23, 2002, pp. 9942-9947, vol. 99, No. 15.
A. Heise et al., Starlike block copolymers with amphiphilic arms as models for unimolecular micelles, J. Am. Chem. Soc. 121 (1999) 8647-8648.

(Continued)

*Primary Examiner* — Dana H Shin
(74) *Attorney, Agent, or Firm* — Foley & Lardner LLP

(57) ABSTRACT

Provided are a unimolecular nanoparticle, a composition thereof, and methods of use thereof, and includes 1) a dendritic polymer having a molecular weight of about 500-120,000 Da and terminating in hydroxyl, amino or carboxylic acid groups; 2) cationic polymers attached to at least a majority of the terminating groups of the dendritic polymer via a pH-sensitive linker, wherein each cationic polymer comprises a polymeric backbone attached to cationic functional groups and to weakly basic groups by disulfide bonds, wherein the molar ratio of cationic functional groups to weakly basic groups ranges from 1:1-5:1, and has a molecular weight from about 1,000-5,000 Da; and 3) poly(ethylene glycol) attached to a plurality of cationic polymers and having a terminal group selected from a targeting ligand, OH, O-alkyl, $NH_2$, biotin, or a dye, wherein the terminal group of at least one poly(ethylene glycol) is having a molecular weight of about 1,000-15,000 Da.

23 Claims, 18 Drawing Sheets

Specification includes a Sequence Listing.

(56) References Cited

OTHER PUBLICATIONS

Arnold et al., "Engineered polymeric nanoparticles to guide the cellular internalization and trafficking of small interfering ribonucleic acids", Journal of Controlled Release, vol. 259, Feb. 21, 2017, URL: http://www.sipcd.com/upload/1503907118588304.pdf, pp. 3-15.

Arvizo, R. et al., "Effect of Nanoparticle Surface Charge at the Plasma Membreane and Beyond", Nano letters 2010, 10, 2543-2548.

Bai, et al., "Simultaneous detection and quantification of mitochondrial DNA deletion(s), depletion, and over-replication in patients with mitochondrial disease," The Journal of Molecular Diagnostics, Nov. 2005, pp. 613-622, vol. 7, Issue 5.

Brumbach et al., "Mixtures of poly(triethylenetetramine/cystamine bisacrylamide) and poly (triethylenetetramine/cystamine bisacrylamide)-g-polyethylene glycol for improved gene delivery", Bioconjugate Chemistry, vol. 21, No. 10, Oct. 20, 2011, URL: https://www.ncbi.nlm.nih.gov/pmc/articles/PMC2958694/pdf/nihms241669.pdf, entire document.

Cardenas, et al., "Selective Vulnerability of Cancer Cells by Inhibition of CA (2) Transfer from Endoplasmic Reticulum to Mitochondria," Cell Reports, Mar. 2016, pp. 2313-2324, vol. 14, Issue 10.

Carlson-Stevermer, J. et al., "Assembly of CRISPR ribonucleoproteins with biotinylated oligonucleotides via an RNA aptamer for precise gene editing", Nature Communications 2017, 8, 1711.

Chen et ai., "A Universal GSH-Responsive Nanoplatform for the Delivery of DNA, mRNA, and Cas9/sgRNA Ribonucleoprotein", ACS Applied Materials & Interfaces, vol. 10, No. 22, Sep. 17, 2018, URL: https://www.ncbi.nlm.nih.gov/pmc/articles/PMC6141193/pdf/nihms-986704.pdf. pp. 1-19.

Christofk, et al., "The M2 splice isoform of pyruvate kinase is important for cancer metabolism and tumour growth," Nature, Mar. 2008, pp. 230-233, vol. 452.

Clayton, et al., "Isolation of mitochondria from tissue culture cells," Cold Spring Harbor Protocols, 2014, pp. 1109-1112.

Frohlich, "The role of surface charge in cellular uptake and cytotoxicity of medical nanoparticles", International Journal of Nanomedicine 2012, 7, 5577-5591.

H. Maeda et al., Analyses of repeated failures in cancer therapy for solid tumors: poor tumor-selective drug delivery, low therapeutic efficacy and unsustainable costs, Clin. Transl. Med. 7 (2018) 11.

Ho, et al., "Phosphoenolpyruvate is a Metabolic Checkpoint of Anti-tumor T Cell Responses," Cell, Sep. 2015, pp. 1217-1228, vol. 162, Issue 6.

International Search Report and Written Opinion in PCT/US2019/019051 dated Apr. 29, 2019 (10 pages).

K.M. Takeda et al., Effect of shear stress on structure and function of polyplex micelles from poly (ethylene glycol)-poly (L-lysine) block copolymers as systemic gene delivery carrier, Biomaterials 126 (2017) 31-38.

Karvelis et al., "Harnessing the natural diversity and in vitro evolution of Cas9 to expand the genome editing toolbox", Current Opinion in Microbiology 2017, 37:88-94.

Komor, A.C. et al. "CRISPR-Based Technologies for the Manipulation of Eukaryotic Genomes", Cell 168:20-36 (2017).

Lee, Y., et al., "Charge-Conversion Ternary Polyplex with Endosome Disruption Moiety: A Technique for Efficient and Safe Gene Delivery", Angewandte Chemie 2008, 120, 5241-5244.

Lunt, et al., "Pyruvate kinase isoform expression alters nucleotide synthesis to impact cell proliferation," Molecular Cell, Jan. 2015, pp. 95-107, vol. 57, Issue 1.

M.J. Lawrence, Surfactant systems: their use in drug delivery, Chem. Soc. Rev. 23 (1994) 417-424.

Minn, et al., "Genes that mediate breast cancer metastasis to lung," Nature, Jul. 2005, pp. 518-524, vol. 436.

Moret, I, et al., "Stability of PEI-DNA and DOTAP-DNA complexes: effect of alkaline pH, heparin and serum", Journal of Controlled Release 2001, 76, 169-181.

Murovec, J. et al., "New variants of CRISPR RNA-guided genome editing enzymes", Plant Biotechnol. J. 15:917-26 (2017).

Non-Final Office Action on U.S. Appl. No. 15/892,140 dated Jul. 1, 2019 (10 pages).

Notice of Allowance on U.S. Appl. No. 15/892,140 dated Jan. 13, 2020 (9 pages).

Oba, M., et al., "Polyplex micelles prepared from u-cholesteryl PEG-polycation block copolymers for systemic gene delivery", Biomaterials 2011, 32, 652-663.

Polysciences, Inc., "N,N'-Cystaminebisacrylamide, Electro Pure™", Oct. 24, 2017, URL: https://web.archive.org/web/20171024092907/http://www.polysciences.com/default/nn-cystaminebisacrylamide-electro-pure.

S. Kim et al., Overcoming the barriers in micellar drug delivery: loading efficiency, in vivo stability, and micelle-cell interaction, Expert Opin. Drug Deliv. 7 (2010) 49-62.

Sanchez, et al., "Genome-wide analysis of the human p53 transcriptional network unveils a lucRNA tumour suppressor signature," Nature Communications, 2014, pp. 1-13, vol. 5.

Sarett, S, et al., "Technologies for controlled, local delivery of siRNA", Journal of Controlled Release 218 (2015), 94-113.

Wang et al., "Versatile Redox-Responsive Polyplexes for the Delivery of Plasmid DNA, Messenger RNA, and CRISPR-Cas9 Genome-Editing Machinery", ACS Applied Materials & Interfaces, 2018, 10, 31915-31927.

Wang et al., "Versatile Redox-Responsive Polyplexes for the Delivery of Plasmid DNA, Messenger RNA, and CRISPR-Cas9 Genome-Editing Machinery", ACS Applied Materials & Interfaces, vol. 10, No. 38, Sep. 17, 2018, URL: https://pubs.acs.org/doi/abs/10.1021/acsami.8b09642, abstract.

Wang Y, Ye M, Xie R, Gong S. Enhancing the In Vitro and In Vivo Stabilities of Polymeric Nucleic Acid Delivery Nanosystems. Bioconjugate chemistry 2018, 30(2): 325-337.

Wang, et al., "CARM1 methylates chromatin remodeling factor BAF155 to enhance tumore progression and metastasis," Cancer Cell, Jan. 2014, pp. 21-26, vol. 25, Issue 1.

Wang, R.E., et al., "A homogeneous fluorescent sensor for human serum albumin", Journal of Pharmaceutical and Biomedical Analysis 2012, 63, 165-169.

X. Sun et al., The blood clearance kinetics and pathway of polymeric micelles in cancer drug delivery, ACS Nano 12 (2018) 6179-6192.

Patil et al., "Multifunctional Triblock Nanocarrier (PAMAM-PEG-PLL) for the Efficient Intracellular siRNA Delivery and Gene Silencing" ACSNANO, vol. 5, No. 3, (2011), pp. 1877-1887.

* cited by examiner

UNIMOLECULAR NANOPARTICLES FOR EFFICIENT DELIVERY OF THERAPEUTIC RNA

CROSS REFERENCE TO RELATED APPLICATION

This application claims the benefit of and priority to U.S. Provisional Application No. 62/426,004 filed Nov. 23, 2016, the contents of which is incorporated herein by reference its entirety.

GOVERNMENT RIGHTS

This invention was made with government support under CA166178 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Sep. 6, 2019, is named 032026-1364_SL.txt and is 12,534 bytes in size.

FIELD

The present technology relates generally to the field of siRNA drug delivery systems and methods of making and using such systems. The compositions of such systems include a unimolecular nanoparticle and siRNA drug(s).

BACKGROUND

Specific silencing of target genes using short interfering RNA (siRNA) is of significant interest for the treatment of cancers and other disease. siRNA molecules are double-stranded short chain oligonucleotides that post-transcriptionally regulate protein synthesis by sequence-specific matching with mRNA molecules, thereby resulting in specific silencing of target genes. Currently, several dozen potential siRNA therapies are undergoing clinical trials. However, due to their negatively charged nature, limited chemical stability, short plasma elimination half-life, and off target effect, naked siRNA molecules show poor therapeutic efficacy. Various viral and non-viral delivery systems have been developed to improve the efficacy of siRNA therapy. Although viral vectors provide high transfection efficiency, concerns associated with insertional mutagenesis, immunogenicity, and cytotoxicity limit their use. Non-viral delivery systems potentially offer a safer and cheaper alternative to viral vectors. Currently there is no clinically available method of siRNA delivery suitable for gene silencing for treatment of diseases such as cancer.

SUMMARY

In one aspect, the present technology provides a unimolecular nanoparticle that includes 1) a dendritic polymer having a molecular weight of about 500 to about 120,000 Da and terminating in hydroxyl, amino or carboxylic acid groups; 2) cationic polymers attached to at least a majority of the terminating groups of the dendritic polymer via a pH-sensitive linker, wherein each cationic polymer comprises a polymeric backbone attached to cationic functional groups and to weakly basic groups by disulfide bonds, wherein the molar ratio of cationic functional groups to weakly basic groups ranges from 1:1 to 5:1, and has a molecular weight from about 1,000 to about 5,000 Da; and 3) poly(ethylene glycol) attached to a plurality of cationic polymers and having a terminal group selected from a targeting ligand, OH, O-alkyl, $NH_2$, biotin, or a dye, wherein the poly(ethylene glycol) has a molecular weight of about 1,000 to about 15,000 Da.

In some embodiments of the unimolecular nanoparticle, the dendritic polymer is a polyester or a poly(amido-amine). The dendritic polymer may be a hyper-branched polymer or a dendrimer. The dendritic polymer may have from 3-7 generations. In some embodiments, the dendritic polymer is a poly(amido-amine) dendrimer having 3 to 4 generations. In other embodiments, the dendritic polymer is a hyper-branched polyester having 3 to 4 generations.

In some embodiments of the unimolecular nanoparticle, the pH-sensitive linker contains an imine, hydrazone or cis-aconityl group.

In some embodiments of the unimolecular nanoparticle, each cationic polymer includes a polyamide backbone, disulfide linkers, amino and/or ammonium groups, and imidazole groups. The polyamide backbone may be, e.g., a polyasparagine, polyglutamine, polyornithine, or polylysine. In some embodiments, the cationic polymers comprises moieties selected from the group consisting of a (C2-6 alkylene)disulfide(C2-C6 alkyl)amino group, a (C2-6 alkylene)disulfide(C2-C6 alkyl)aminocarbonylimidazole group, and salts thereof. In certain embodiments, the cationic polymers comprise moieties selected from the group consisting of ethylene-disulfide-ethylamino group, ethylene-disulfide-ethylaminocarbonylimidazole group and salts thereof.

In some embodiments of the unimolecular nanoparticle, the targeting ligand is a cofactor, carbohydrate, peptide, antibody, nanobody, or aptamer. For example, the targeting ligand may be selected from the group consisting of folic acid, mannose, GE11, cRGD, KE108, octreotide, TAT cell penetrating peptide, PSMA aptamer, TRC105, 7D12 nanobody, CTB.

In some embodiments, the unimolecular nanoparticle includes a therapeutic RNA within the nanoparticle. The therapeutic RNA may be an siRNA. The loading of the siRNA may be about 1 to about 20 wt % of the unimolecular nanoparticle.

In some embodiments of the unimolecular nanoparticle, the dendritic polymer is a hyperbranched polyester having 3-4 generations and a molecular weight of about 3,600 to about 7,400 Da; the pH-sensitive linker is a benzylimine; each cationic polymer has a polyasparagine backbone attached to an ethylene-disulfide-ethylamino or ethylene-disulfide-ethylaminocarbonylimidazole group or salt thereof, and the molar ratio of the amino to imidazole functional groups is from 1:1 to 5:1; and the molecular weight of the PEG is about 1,000 to about 15,000 Da.

In another aspect, the present technology provides a method of preparing a unimolecular nanoparticle comprising dispersing therapeutic RNA within any unimolecular nanoparticle described herein In another aspect, the present technology provides compositions comprising a unimolecular nanoparticle as described herein and a pharmaceutically acceptable carrier.

In one aspect, the present technology provides methods of treating a cancer by administering an effective amount of a unimolecular nanoparticle as described herein loaded with a therapeutic RNA, wherein the therapeutic RNA inhibits expression of a gene necessary for survival or growth of the cancer. In some embodiments of the method, therapeutic RNA is siRNA having a length of 19 base pairs (bps) to 25 bps.

In another aspect, the present technology provides a kit comprising a package containing a unimolecular nanoparticle as described herein and a package containing an effective amount of therapeutic siRNA and directions for use of the kit.

DETAILED DESCRIPTION

Figure 1:
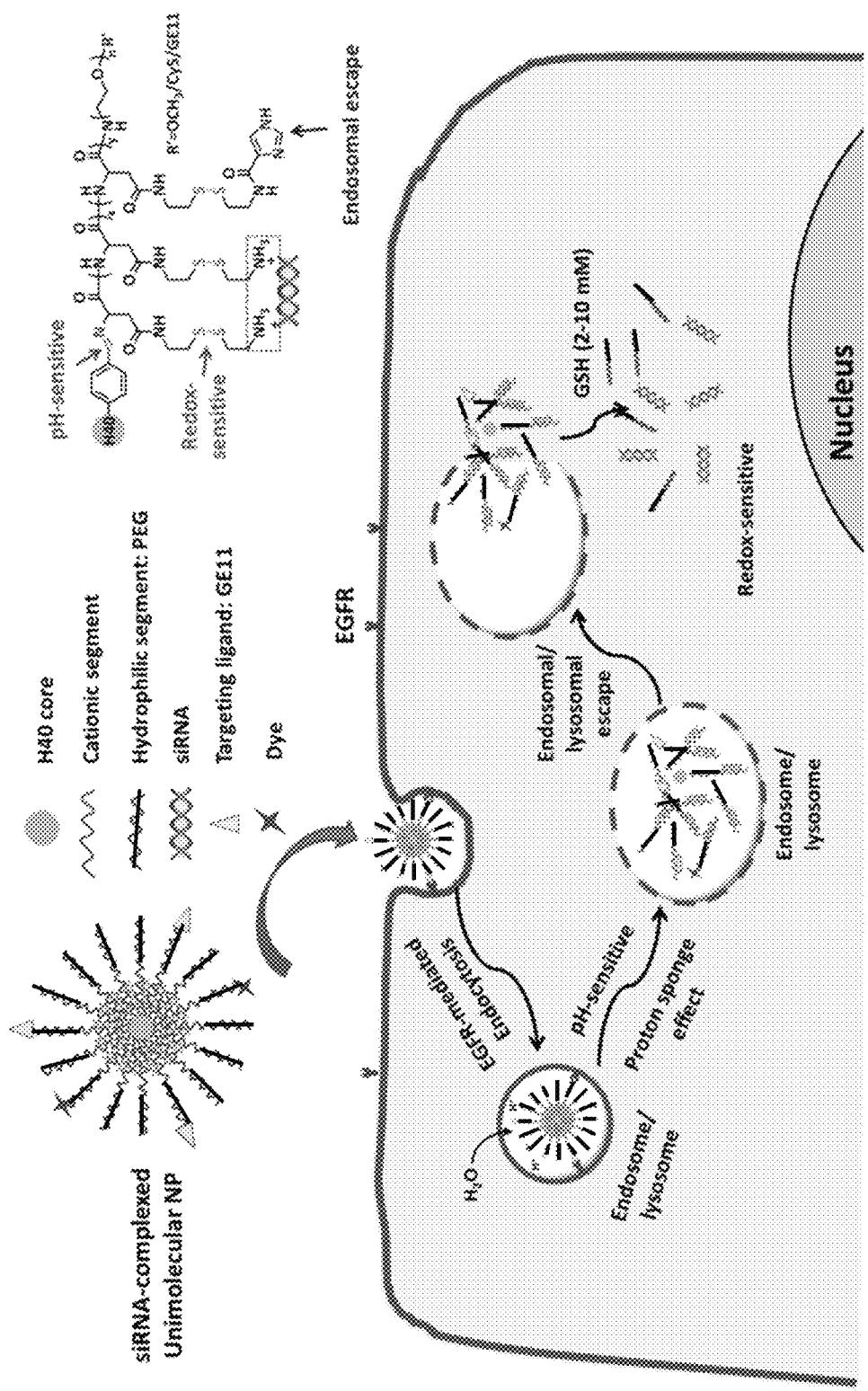
FIG. 1 shows a schematic diagram of the cellular uptake of siRNA-complexed unimolecular NPs and the subcellular release of siRNA from the siRNA-complexed NPs into the cytosol. pH/redox dual-sensitive unimolecular NPs with excellent endosomal/lysosomal escape and intracellular siRNA decomplexation capabilities for efficient targeted delivery of siRNA.

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

"Molecular weight" as used herein with respect to polymers refers to weight average molecular weights (Mw) and can be determined by techniques well known in the art including gel permeation chromatography (GPC). GPC analysis can be performed, for example, on a D6000M column calibrated with poly(methyl methacrylate) (PMMA) using triple detectors including a refractive index (RI) detector, a viscometer detector, and a light scattering detector, and dimethylformamide as the eluent.

The terms "cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this disclosure apply to malignant, pre-metastatic, metastatic, and non-metastatic cells.

The term "therapeutic RNA" refers to single strand or duplex RNA that modulates (e.g., silences, reduces, or inhibits) expression of a target gene, e.g., by mediating the degradation of mRNAs which are complementary to the sequence of the interfering RNA, by providing an RNA that is absent or expressed at a lower level in a subject having a particular disease or condition relative to its levels in a subject that does not have the same disease or condition. Examples of therapeutic RNAs include siRNA and miRNA.

The term "small-interfering RNA" or "siRNA" refers to double-stranded RNA (i.e., duplex RNA) that modulates (e.g., silences, reduces, or inhibits) expression of a target gene, e.g., by mediating the degradation of mRNAs which are complementary to the sequence of the siRNA. Typically, siRNA has complete identity or complementarity to the corresponding RNA sequence of its target mRNA. siRNA includes RNA of having 15-60, 15-50, 15-50, or 15-40 (duplex) nucleotides in length, more typically about, 15-30, 15-25 or 19-25 (duplex) nucleotides in length, and may be 20-24, 21-22 or 21-23 (duplex) nucleotides in length. siRNA duplexes may include 3' overhangs of 1, 2, 3, or 4 nucleotides and/or 5' phosphate termini. The siRNA can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., PNAS USA 99: 9942-7

(2002); Calegari et al., PNAS USA 99: 14236 (2002); Byrom et al., Ambion TechNotes 10(1): 4-6 (2003); Kawasaki et al., Nucleic Acids Res. 31: 981-7 (2003); Knight and Bass, Science 293: 2269-71 (2001); and Robertson et al., J. Biol. Chem. 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

The phrase "inhibits expression of a gene" refers to the ability of a therapeutic RNA, such as an siRNA, of the technology to silence, reduce, or inhibit expression of a target gene (e.g., VEGF, EphA2, protein kinase N3 (PKN3), etc.). To examine the extent of gene silencing, a test sample (e.g., a biological sample from organism of interest expressing the target gene or a sample of cells in culture expressing the target gene) is contacted with an siRNA that silences, reduces, or inhibits expression of the target gene. Expression of the target gene in the test sample is compared to expression of the target gene in a control sample (e.g., a biological sample from organism of interest expressing the target gene or a sample of cells in culture expressing the target gene) that is not contacted with the siRNA. Control samples (i.e., samples expressing the target gene) are assigned a value of 100%. Silencing, inhibition, or reduction of expression of a target gene is achieved when the value of the test sample relative to the control sample is about 95%, 90%, 85%, 80%, 75%, 70%, 65%, 60%, 55%, 50%, 45%, 40%, 35%, 30%, 25%, 20%, 10%, 0% or a range between and including any two of the foregoing values. Suitable assays include, e.g., examination of mRNA levels using techniques known to those of skill in the art such as dot blots, northern blots, in situ hybridization, ELISA, immunoprecipitation, enzyme function, as well as phenotypic assays known to those of skill in the art.

The phrase "a targeted receptor" refers to a receptor expressed by a cell that is capable of binding a cell targeting ligand. The cell targeting ligand may be a "tumor cell targeting ligand." The receptor may be expressed on the surface of the cell. The receptor may be a transmembrane receptor. Examples of such targeted receptors include EGFR, $\alpha_v\beta_3$ integrin, somatostatin receptor, folate receptor, prostate-specific membrane antigen, CD105, mannose receptor, and GM1 ganglioside.

The phrase "tumor cell targeting ligand" refers to a ligand that binds to "a targeted receptor" unique to or overexpressed by a cancer cell. The ligands may be capable of binding due to preferential expression of a receptor for the ligand, accessible for ligand binding, on the cancer cells. Examples of such ligands include GE11 peptide, cRGD ((cyclo (RGDfC)), KE108 peptide, octreotide, folic acid, prostate-specific membrane antigen (PSMA) aptamer, TRC105, a human/murine chimeric IgG1 monoclonal antibody, 7D12 nanobody, mannose, and cholera toxin B (CTB). Additional examples of such ligands include Rituximab, Trastuzumab, Bevacizumab, Alemtuzumab, Panitumumab, RGD, DARPins, RNA aptamers, DNA aptamers, analogs of folic acid and other folate receptor-binding molecules, lectins, other vitamins, peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selecting, steroid hormones, Arg-Gly-Asp containing peptides, retinoids, various galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of tumor cells or on an infectious organism, or fragments of any of these molecules.

In some embodiments, a cell penetrating peptide may also be attached to one or more PEG terminal groups in addition to the targeting ligand. A "cell penetrating peptide," also referred to as a "protein transduction domain (PTD)," a "membrane translocating sequence," and a "Trojan peptide", refers to a short peptide (e.g., from 4 to about 40 amino acids) that has the ability to translocate across a cellular membrane to gain access to the interior of a cell and to carry into the cells a variety of covalently and noncovalently conjugated cargoes, including proteins, oligonucleotides, and liposomes. They are typically highly cationic and rich in arginine and lysine amino acids. Examples of such peptides include TAT cell penetrating peptide (GRKKRRQRRRPQ (SEQ ID NO: 1)); MAP (KLAL) KLALKLALKAL-KAALKLA (SEQ ID NO: 2); Penetratin or Antenapedia PTD RQIKWFQNRRMKWKK (SEQ ID NO: 3); Penetratin-Arg: RQIRIWFQNRRMRWRR (SEQ ID NO: 4); anti-trypsin (358-374): CSIPPEVKFNKPFVYLI (SEQ ID NO: 5); Temporin L: FVQWFSKFLGRIL-NH$_2$ (SEQ ID NO: 6); Maurocalcine: GDC(acm)LPHLKLC (SEQ ID NO: 7); pVEC (Cadherin-5): LLIILRRRIRKQAHAHSK (SEQ ID NO: 8); Calcitonin: LGTYTQDFNKFHTFPQTAIGVGAP (SEQ ID NO: 9); Neurturin: GAAEAAARVYDLGLRRLRQRRRLRRERVRA (SEQ ID NO: 10); Penetratin: RQIKIWFQNRRMKWKKGG (SEQ ID NO: 11); TAT-HA2 Fusion Peptide: RRRQRRKKRGGDIMGEWGNEIFGAIAGFLG (SEQ ID NO: 12); TAT (47-57) YGRKKRRQRRR (SEQ ID NO: 13); SynB1 RGGRLSYSRRRFSTSTGR (SEQ ID NO: 14); SynB3 RRLSYSRRRF (SEQ ID NO: 15); PTD-4 PIRRRKKLRRL (SEQ ID NO: 16); PTD-5 RRQRRTSK-LMKR (SEQ ID NO: 17); FHV Coat-(35-49) RRRRNR-TRRNRRRVR (SEQ ID NO: 18); BMV Gag-(7-25) KMTRAQRRAAARRNRWTAR (SEQ ID NO: 19); HTLV-II Rex-(4-16) TRRQRTRRARRNR (SEQ ID NO: 20); HIV-1 Tat (48-60) or D-Tat GRKKRRQRRRPPQ (SEQ ID NO: 21); R9-Tat GRRRRRRRRRPPQ (SEQ ID NO: 22); Transportan GWTLNSAGYLLGKINLKALAALAKKIL (SEQ ID NO: 23) chimera; MAP KLALKLALKLALA-LKLA (SEQ ID NO: 24); SBP or Human P1 MGLGLHLL-VLAAALQGAWSQPKKKRKV (SEQ ID NO: 25); FBP GALFLGWLGAAGSTMGAWSQPKKKRKV (SEQ ID NO: 26); MPG ac-GALFLGFL-GAAGSTMGAWSQPKKKRKV-cya (SEQ ID NO: 27) (wherein cya is cysteamine); MPG(ΔNLS) ac-GALFLGFL-GAAGSTMGAWSQPKSKRKV-cya (SEQ ID NO: 28); Pep-1 or Pep-1-Cysteamine ac-KETWWETWWTEWS-QPKKKRKV-cya (SEQ ID NO: 29); Pep-2 ac-KETWFETWFTEWSQPKKKRKV-cya (SEQ ID NO: 30); Periodic sequences, Polyarginines RxN (4<N<17) (SEQ ID NO: 31) chimera; Polylysines KxN (4<N<17) (SEQ ID NO: 32) chimera; (RAca)6R (SEQ ID NO: 33); (RAbu)6R (SEQ ID NO: 34); (RG)6R (SEQ ID NO: 35); (RM)6R (SEQ ID NO: 36); (RT)6R (SEQ ID NO: 37);

(RS)6R (SEQ ID NO: 38); R10 (SEQ ID NO: 39); (RA)6R (SEQ ID NO: 40); and R7 (SEQ ID NO: 41).

A "dye" refers to small organic molecules having a molecular weight of 2000 Da or less or a protein which is able to emit light. Non-limiting examples of dyes include fluorophores, chemiluminescent or phosphorescent entities. For example, dyes useful in the present technology include but are not limited to cyanine dyes (e.g., Cy2, Cy3, Cy5, Cy5.5, Cy7, and sulfonated versions thereof), fluorescein isothiocyanate (FITC), ALEXA FLUOR® dyes (e.g., ALEXA FLUOR® 488, 546, or 633), DYLIGHT® dyes (e.g., DYLIGHT® 350, 405, 488, 550, 594, 633, 650, 680, 755, or 800) or fluorescent proteins such as GFP (Green Fluorescent Protein).

The present technology provides pharmaceutical compositions and medicaments comprising any of one of the embodiments of the siRNA delivery systems disclosed herein and a pharmaceutically acceptable carrier or one or more excipients. The compositions may be used in the methods and treatments described herein. In one aspect the present technology provides a drug delivery system for the prevention or treatment of cancer. The pharmaceutical composition may include an effective amount of any of one of the embodiments of the compositions disclosed herein. In any of the above embodiments, the effective amount may be determined in relation to a subject. "Effective amount" refers to the amount of compound or composition required to produce a desired effect. One example of an effective amount includes amounts or dosages that yield acceptable toxicity and bioavailability levels for therapeutic (pharmaceutical) use including, but not limited to, the inhibition (i.e., slowing, halting or reversing) or treatment of cancer in a subject. As used herein, a "subject" or "patient" is a mammal, such as a cat, dog, rodent or primate. Typically the subject is a human, and, preferably, a human at risk for or suffering from cancer. The term "subject" and "patient" can be used interchangeably. An effective amount of a therapeutic RNA, such as an siRNA or a therapeutically effective amount of a siRNA is an amount sufficient to produce the desired effect, e.g., a decrease in the expression of a target sequence in comparison to the normal expression level detected in the absence of the siRNA.

In one aspect, the present technology provides unimolecular nanoparticles designed to deliver therapeutic RNA selectively to tumor cells. The RNA is protected within the nanoparticles until it reaches the cytoplasm of the targeted cell. The technology employs a unique combination of pH sensitive and redox sensitive functionality to release the RNA intact from the nanoparticles only once the nanoparticles are within the targeted cells.

The present unimolecular nanoparticles include three distinct polymeric domains: a dendritic polymer, which serves as the core, cationic polymers attached to the terminal groups of the dendritic polymer and PEG, attached to the terminal groups of the cationic polymers. Thus, the unimolecular nanoparticle may be described as a multi-arm star-like block copolymer. Therapeutic RNA, such as siRNA or miRNA may be loaded into the unimolecular nanoparticles described herein. While not wishing to be bound by theory, it is believed that the therapeutic RNA is bound by electrostatic interactions with the cationic polymers on the interior of the nanoparticle.

The dendritic polymer has a molecular weight of about 500 to about 120,000 Da and terminates in hydroxyl, amino or carboxylic acid groups. The molecular weight of the dendritic polymer will vary based on the type of polymer and number of generations employed. Suitable molecular weights include about 500, about 1000, about 2000, about 3000, about 4000, about 5000, about 6000, about 7000, about 8000, about 9000, about 10,000, about 15,000, about 20,000, about 30,000, about 40,000, about 50,000, about 75,000, about 100,000, about 120,000 Da, or a range between and including any two of the forgoing values. In some embodiments the molecular weight of the dendritic polymer is about 1,000 to about 10,000 Da. The core of the unimolecular nanoparticle may be a dendrimer such as a poly(amido-amine) (PAMAM) dendrimer having from 3 to 7 generations (e.g., 3, 4, 5, 6, or 7 generations or a range between and including any two of the foregoing values) or a hyperbranched polymer such as a polyester hyperbranched polymer (e.g., Boltorn H30 and H40, which are prepared from 2,2-bis(methylol)propionic acid). PAMAM will be understood to refer to a polymer having a $C_2$-$C_4$ α, ω-diamine initiator and $C_3$-$C_4$ acrylate and diamine building blocks for each subsequent generation. Typically the building blocks are $C_2$ 1,2-diamines and $C_3$ acrylates (not counting the methyl ester carbon, which serves as a temporary protecting group). In some embodiments, the PAMAM dendrimer has from 3 to 4 generations. In some embodiments, the dendritic polymer is a hyperbranched polyester having 3 to 4 generations. The number of generations will determine the number of arms available for attachment to the cationic polymers. Although not every arm of the dendritic polymer must terminate in amino, hydroxyl, carboxylic acid groups, the majority of arms of the dendritic polymer do, e.g., more than 50%, more than 60%, more than 70%, more than 80% or more than 90% of arms of the dendritic polymer terminate in amino, hydroxyl, or carboxylic acid groups. In some embodiments, e.g., where the dendritic polymer is PAMAM, all of the arms terminate in amino groups, hydroxyl groups, or carboxylic acid groups.

The cationic polymers of the unimolecular nanoparticle link the core dendritic polymer to the outer poly(ethylene glycol) (PEG) blocks. The cationic polymers of the unimolecular nanoparticles are attached to at least a majority of the terminating groups of the dendritic polymer via a pH-sensitive linker. The pH-sensitive linker includes a functional group which is readily hydrolyzed upon a change from alkaline pH to acid pH. In some embodiments the pH-sensitive linker will be stable at the pH of blood (about 7.4) and extracellular space in tissue, but hydrolyze at the lower pH of the endosome or lysosome (about 5.5-6.5). Suitable pH-sensitive linkers include imine (e.g., benzylimine), hydrazone and cis-aconityl linkers. While not wishing to be bound by theory, hydrolysis of the pH-sensitive linker is intended to release the block cationic-PEG copolymer from the dendritic core upon a change in pH from alkaline to acid.

Each cationic polymer is made up of a polymeric backbone attached to cationic functional groups and to weakly basic groups by redox-sensitive linkers that include disulfide bonds. The polymeric backbone may be a polyamide backbone such as a found in peptides and proteins. In some embodiments the polyamide is a polyasparagine, polyglutamine, polyornithine, or polylysine. The cationic functional groups may be functional groups having a pka of at least about 8 (e.g., a pka of 8, 8.5, 9, 9.5, 10, 10.5, 11 or a range between and including any two of the foregoing values). Suitable groups include primary, secondary and tertiary amines, amidines, and guanidines. It will be understood that the cationic functional groups may be attached to the side-chains of the polyamide backbone. For example aspartic acid and glutamic acid side chains may be derivatized with disulfides formed from aminoalkylenethiols: (polyamide backbone)-CH$_2$CH$_2$—C(O)NH—(C1-6 alkylene)-S—S—(C1-C6 alkylene)-NH$_2$), or (polyamide backbone)-CH$_2$—C(O)NH—(C1-6 alkylene)-S—S—(C1-C6 alkylene)-NH$_2$). When derivatized in this fashion, it will be understood that the polyaspartic acid or polyglutamic acid are now a polyasparagine or a polyglutamine, respectively. Similarly, polyornithine and polylysine may be attached to cationic functional groups through suitably functionalized species such as carboxy-alkylene-disulfide-alkylene-amino groups, e.g., (polyamide backbone)-CH$_2$CH$_2$—CHNH—C(O)—(C1-6 alkylene)-S—S—(C1-C6 alkylene)-NH$_2$), or (polyamide backbone)-CH$_2$CH$_2$CH$_2$NH—C(O)—(C1-6 alkylene)-S—S—(C1-C6 alkylene)-NH$_2$).

Weakly basic groups useful in the unimolecular nanoparticles may have a pKa between about 5.5 and about 7.0, e.g., a pKa of 5.5, 5.75, 6, 6.25, 6.5, 6.75, 7, or a range between and including any two of the foregoing values. In some embodiments, the weakly basic group is imidazole or pyridinyl. In certain embodiments, the molar ratio of cationic functional groups to weakly basic groups ranges from 1 to 5; in others it is 2 to 4. Suitable molar ratios include about 1, about 2, about 3, about 4, and about 5 or a range between and including any two of the foregoing values.

In certain embodiments, the cationic polymer has a molecular weight from about 1,000 to about 5,000 Da; in others it is about 1,500 to about 4,000 Da. Suitable molecular weights for the cationic polymers include about 1,000, about 1,500, about 2,000, about 2,500, about 3,000, about 3,500, about 4,000, about 4,500, about 5,000 or a range between and including any two of the foregoing values.

In some embodiments, each cationic polymer comprises a polyamide backbone, disulfide linkers, amino groups, and imidazole groups. In some embodiments, the cationic polymers comprise moieties selected from the group consisting of (C2-6 alkylene)disulfide(C2-C6 alkyl)amino group, (C2-6 alkylene)disulfide(C2-C6 alkyl)aminocarbonylimidazole group, and salts thereof. the cationic polymers comprise moieties selected from the group consisting of ethylenedisulfide-ethylamino group, ethylene-disulfide-ethylaminocarbonylimidazole group and salts thereof.

PEG is a hydrophilic polymer that forms the outer layer of the unimolecular nanoparticle. The PEG polymeric blocks are attached to a plurality of the cationic polymers. Each arm of the PEG terminates in one of various groups selected from a targeting ligand, OH, O—(C1-C6)alkyl, NH$_2$, biotin or a dye. In some embodiments the PEG terminates in OH or O—(C1-C6)alkyl, and in still others the PEG terminates in in an OC$_{1-3}$ alkyl group. In still other embodiments, the PEG terminates in a targeting ligand. The targeting ligand may be selected from the group consisting of a cofactor, carbohydrate, peptide, antibody, nanobody, or aptamer. In other embodiments, the targeting ligand is selected from the group consisting of folic acid, mannose, GE11, cRGD, KE108, octreotide, TAT cell penetrating peptide, PSMA aptamer, TRC105, 7D12 nanobody, and CTB.

Typically each arm of the PEG has 23 to 340 repeat units or a molecular weight of about 1,000 to about 15,000 Da. Suitable molecular weights for each PEG block of the unimolecular nanoparticle include about 1,000, about 1,500, about 2,000, about 2,500, about 3,000, about 4,000, about 5,0000, about 7,500, about 10,000, or about 15,000 Da, or a range between and including any two of the foregoing values.

In another aspect, the unimolecular nanoparticle includes a therapeutic RNA within the nanoparticle, such as an siRNA. In some embodiments, the loading of the siRNA is about 1 to about 20 wt % of the unimolecular nanoparticle. For example, the loading of the siRNA may be about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt % or a range between and including any two of the foregoing values.

Any therapeutic RNA may be used in the present unimolecular nanoparticle drug delivery systems. While not wishing to be bound by theory, it is believed that the cationic polymers of the unimolecular nanoparticle bind the therapeutic RNA via electrostatic interactions between the negatively charged phosphate backbone of the therapeutic RNA and the cationic functional groups of the cationic polymers. Hence, loading of the therapeutic RNA is independent of the base sequence of the RNA. Likewise, therapeutic RNA of a variety of sequence lengths may be loaded into the unimolecular nanoparticle. In some embodiments, the length of the therapeutic RNA is 20, 21, 22, 23 or 24 bps or a range between and including any two of the foregoing values. In certain embodiments, the length of the therapeutic RNA is from about 21 to about 23 bps.

In some embodiments, the therapeutic RNA loaded in the unimolecular nanoparticle is an siRNA that inhibits expression of a gene necessary for survival or growth of a cancer. The gene necessary for survival or growth of the cancer may be selected from oncogenes, mutated tumor suppressor genes, and genes involved in tumor progression and cell cycle progression. In certain embodiments, the siRNAs interfere with transcription of genes for VEGF, EphA2, protein kinase N3 (PKN3), PLK1, KSP, ribonucleotide reductase regulatory subunit M2 (RRM2), gro-α, MDR-1, androgen receptor (AR), acid ceramidase (AC), HIF1, CDK4, GATA2, and the like. In some embodiments, the length of the siRNA is 20, 21, 22, 23 or 24 bps or a range between and including any two of the foregoing values. In certain embodiments, the length of the siRNA is from about 21 to about 23 bps.

The unimolecular nanoparticles may be prepared using standard techniques. For example, a dendritic polymer in which most or all of the surface arms terminate in amino, hydroxyl, or carboxylic acid groups may be conjugated to the cationic polymers via amide, ester, or ether groups. Typically, ester and amide linkages are used for ease of formation. Likewise, the PEG blocks may be attached to the cationic polymers via ester, amide or ether groups. In some embodiments, the PEG has a hydroxy group on one end and an alkoxy or carbonylalkoxy on the other. Standard coupling conditions such as the use of tin catalysis or coupling agents or active esters may be used to form the ester or amide bonds.

The unimolecular nanoparticles described herein may be used to treat, inhibit or prevent cancer by administering an effective amount of the unimolecular nanoparticle wherein the siRNA inhibits expression of a gene necessary for survival or growth of the cancer.

The compositions described herein can be formulated for various routes of administration, for example, by parenteral, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the nanoparticles described herein. Injectable forms may be prepared with acceptable solvents or vehicles including, but not limited to sterilized water, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the siRNA drugs to the patient and may include about 0.1 mg/kg, about 0.2 mg/kg, about 0.3 mg/kg, about 0.4 mg/kg, about 0.5 mg/kg, about 0.75 mg/kg, about 1 mg/kg, about 1.25 mg/kg, about 1.5 mg/kg, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

The nanoparticles described herein may be prepared by methods comprising dispersing the siRNA within the unimolecular nanoparticle. The drug delivery systems include compositions comprising unimolecular nanoparticles dispersed within a pharmaceutically acceptable carrier or one or more excipients, and an effective amount of anti-cancer siRNA dispersed within the unimolecular nanoparticle. As used herein, "dispersed" means distributed, in a generally uniform or in a non-uniform fashion. In some embodiments, the siRNA is dispersed in a generally uniform fashion within the nanoparticle. However, it will be understood that nanoparticles with a non-uniform distribution of siRNA, especially those with small variations in concentration of the siRNA are within the scope of the present technology. The anti-cancer siRNA may also be non-uniformly distributed within the unimolecular nanoparticles.

In another aspect, the present technology provides kits including the components needed to prepare any of the compositions described herein. For example, a kit may include a package containing a unimolecular nanoparticle and a package containing an effective amount of siRNA and directions for use of the kit. In such kits, the unimolecular nanoparticle may include any of those described herein and any of the siRNAs described herein. In some embodiments, the kits may include separate packages for the unimolecular nanoparticles and siRNAs. The present kits allow the user to prepare the drug delivery composition described herein by dispersing the siRNA in the unimolecular nanoparticles.

The examples herein are provided to illustrate advantages of the present technology and to further assist a person of ordinary skill in the art with preparing or using the nanoparticle compositions of the present technology. To the extent that the compositions include ionizable components, salts such as pharmaceutically acceptable salts of such components may also be used. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

The present technology describes a pH/redox dual-sensitive cationic unimolecular NP containing imidazole residues developed for siRNA delivery (FIG. 1). The unimolecular NP was formed by a multi-arm star block copolymer, H40-poly(aspartic acid-(2-aminoethyl disulfide)-(4-imidazolecarboxylic acid))-poly(ethylene glycol) (i.e., H40-P(Asp-AED-ICA)-PEG), in an aqueous solution. Because of its covalent nature, the unimolecular NP has excellent stability in vitro and in vivo. The cationic core formed by P(Asp-AED-ICA) blocks was used for siRNA complexation through electrostatic interactions while the PEG shell was used to provide good water solubility and reduced opsonization of NPs during blood circulation. NPs are taken up by cells through endocytosis. The imidazole groups in the cationic segment have a $pK_a$ of ~6.0 and can thus absorb protons in the acidic endocytic compartments (endosomes/lysosomes), leading to osmotic swelling and endosome/lysosome-membrane disruption (i.e., the proton sponge effect), thereby facilitating the endosomal/lysosomal escape of the siRNA-complexed NPs. Moreover, siRNA molecules were complexed within the NPs by an electrostatic interaction with a cationic P(Asp-AED-ICA) block containing cleavable disulfide bonds. The cationic segments were conjugated onto the hyperbranched polymer (H40) via a pH-sensitive aromatic imine bond, which can be hydrolyzed in the endosome/lysosome, but stays relatively stable at physiological conditions (pH 7.4). Furthermore, once inside the cells, it was expected that the pendant mercaptoethylamine group ($SH-CH_2-CH_2-NH_2$) would be cleaved from the P(Asp-AED-ICA) block by highly concentrated GSH (2-10 mM) in the cytosol. The GSH concentration in the cytosol is 100-1000 times higher than that in bodily fluids, including blood and extracellular milieu (2-20 μM GSH) where the disulfide bonds are stable. The enzyme, gamma-interferon-inducible lysosomal thiol reductase (GILT in the endosomes/lysosomes), in combination with cysteines, may also trigger the cleavage of disulfide bonds. Hence, the pH/redox dual-sensitive characteristic of the NPs may facilitate the release of siRNA from the NPs. The NPs were also functionalized with GE11 peptide, which can efficiently bind to the epidermal growth factor receptor (EGFR) to achieve active tumor targeting. EGFR is one of the most common receptors overexpressed in many types of cancer cells, including triple negative breast cancers (TNBCs), ovarian cancers, pancreatic cancers, and so on. These pH/redox dual-sensitive unimolecular NPs, with excellent endosomal/lysosomal escape abilities, may be promising nanocarriers for the targeted delivery of siRNA.

Example 1: Preparation of siRNA-Loaded Unimolecular Nanoparticle

Materials. BOLTRON® H40 (a hyperbranched polyester with 64 hydroxyl terminal groups; $M_n$: 2,833 Da) was kindly provided by Perester Polyols Inc., USA, and purified by fractional precipitation in acetone and tetrahydrofuran (THF). β-Benzyl 1-aspartate N-carboxyanhydride (BLA-NCA) was prepared as previously reported. See M. Prabaharan, J. J. Grailer, S. Pilla, D. A. Steeber, S. Gong, Amphiphilic multi-arm-block copolymer conjugated with doxorubicin via pH-sensitive hydrazone bond for tumor-targeted drug delivery, Biomaterials, 30 (2009) 5757-5766. The heterobifunctional poly(ethylene glycol) (PEG) derivatives, methoxy-PEG-NH$_2$ (OCH$_3$—PEG-OH, M$_n$=5 kDa) and maleimide-PEG-NH$_2$ (Mal-PEG-NH$_2$, M$_n$=5 kDa), were purchased from JenKem Technology (Allen, Tex., USA). Cy5 dye was obtained from Lumiprobe Corporation (Hallandale Beach, Fla., USA). GE11 peptide (YHWYGYTPQNVIGGGGC) (SEQ ID NO: 42) was synthesized by Tufts University Core Facility (Boston, Mass., USA). GFP-siRNA-Cy5.5, GFP-siRNA, dimethyl sulfoxide (DMSO), 2-carboxybenzylaldehyde, 2-aminoethyl disulfide, 4-imidazolecarboxylic acid, and stannous (II) octoate (Sn(Oct)$_2$) were purchased from Sigma-Aldrich (St. Louis, Mo., USA). 4-Dimethylamino pyridine (DMAP) and 1,3-dicyclohexylcarbodiimide (DCC) were purchased from ACROS and used without further purification. Other reagents, including RNAiMAX, were purchased from Thermo Fisher Scientific (Fitchburg, Wis., USA) and used as received unless otherwise stated.

Synthesis of H40-Poly(Aspartic Acid-(2-Aminoethyl Disulfide)-(4-Imidazolecarboxylic Acid))-Poly(Ethylene Glycol)-OCH$_3$/Cy5/GE11 (i.e., H40-P(Asp-AED-ICA)-PEG-OCH$_3$/Cy5/GE11)

Synthesis of poly(β-benzyl 1-aspartate N-carboxyanhydride)-poly(ethylene glycol)-Mal (i.e., P(BLA-NCA)-PEG-Mal). P(BLA-NCA)-PEG-Mal was prepared by ring-opening polymerization of BLA-NCA using NH$_2$-PEG-Mal as the macro-initiator. Briefly, BLA-NCA (53 mg), and NH$_2$-PEG-Mal (25 mg) were dissolved in DMF (5 mL). The reaction was carried out at 55° C. under argon for 48 h. The resulting mixture was then added dropwise into a 10-fold volume of cold diethyl ether. The precipitate was collected by filtration using a Büchner funnel, washed with diethyl ether, and dried under vacuum. The P(BLA-NCA)-PEG-OCH$_3$ was synthesized following a similar method using NH$_2$-PEG-OCH$_3$ instead.

Synthesis of H40-carboxybenzaldehyde (i.e., H40-CHO). H40-OH (10 mg), 2-carboxybenzylaldehyde (82 mg), DCC (135 mg), and DMAP (8.3 mg) were dissolved in anhydrous DMSO (3 mL). The solution was stirred at room temperature under argon for 48 h. Thereafter, the dicyclohexylurea was removed by filtration using a Büchner funnel. The solution was collected and poured into a 10-fold volume of cold diethyl ether. The precipitate was collected by filtration using a Büchner funnel, washed with diethyl ether, and dried under vacuum.

Synthesis of H40-poly(β-benzyl 1-aspartate N-carboxyanhydride)-poly(ethylene glycol)-OCH$_3$/Mal (i.e., H40-P(BLA-NCA)-PEG-OCH$_3$/Mal). H40-CHO (5 mg), P(BLA-NCA)-PEG-OCH$_3$ (25 mg), and P(BLA-NCA)-PEG-Mal (8 mg) were dissolved in DMSO. The reaction was conducted at room temperature for 24 h. Thereafter, the resulting solution was dialyzed (molecular weight cut-off: 15 kDa) against DMSO for the first 24 h and DI water for another 24 h. The product was obtained after lyophilization. The H40-P(BLA-NCA)-PEG-OCH$_3$ was synthesized following a similar method.

Synthesis of H40-poly(aspartic acid-(2-aminoethyl disulfide))-poly(ethylene glycol)-OCH$_3$/Mal (i.e., H40-P(Asp-AED)-PEG-OCH$_3$/Mal). 2-Aminoethyl disulfide (13.1 mg) and H40-P(BLA-NCA)-PEG-OCH$_3$/Mal (20 mg) were dissolved in DMSO (10 mL). The reaction was carried out at room temperature for 24 h. Thereafter, the resulting solution was dialyzed (molecular weight cut-off: 15 kDa) against DI water for 48 h. The product was obtained after lyophilization. The H40-P(Asp-AED)-PEG-OCH$_3$ was synthesized following a similar method.

Synthesis of H40-poly(aspartic acid-(2-aminoethyl disulfide)-(4-imidazolecarboxylic acid))-poly(ethylene glycol)-OCH$_3$/Mal (i.e., H40-P(Asp-AED-ICA)-PEG-OCH$_3$/Mal). 4-Imidazolecarboxylic acid (2.2 mg), H40-P(Asp-AED)-PEG-OCH$_3$/Mal (20 mg), DCC (4.4 mg), and N-hydroxysuccinimide (2.9 mg) were dissolved in DMSO (5 mL). The reaction was carried out at room temperature for 24 h. Thereafter, the resulting solution was dialyzed (molecular weight cut-off: 15 kDa) against DI water for 48 h. The product was obtained after lyophilization. The H40-(Asp-AED-ICA)-PEG-OCH$_3$ was synthesized following a similar method.

Synthesis of H40-poly(aspartic acid-(2-aminoethyl disulfide)-(4-imidazolecarboxylic acid))-polyethylene glycol)-OCH$_3$/GE11 (i.e., H40-(PAsp-AED-ICA)-PEG-OCH$_3$/Cy5/GE11). Cy5-SH was first prepared by a reaction between Cy5-NH$_2$ and Traut's reagent. Briefly, Cy5-NH$_2$ (0.3 mg) and Traut's reagent (0.51 mg) were dissolved in DMSO. The solution was stirred at room temperature in complete darkness for 4 h. H40-P(Asp-AED-ICA)-PEG-OCH$_3$/Mal (20 mg) and GE11 (1.3 mg) were added into the above solution. After 24 h, the reaction solution was dialyzed (molecular weight cut-off: 15 kDa) against DI water for 48 h. The product was obtained after lyophilization. The H40-P(Asp-AED-ICA)-PEG-OCH$_3$/Cy5 and H40-P(Asp-AED-ICA)-PEG-OCH$_3$/GE11 were synthesized following a similar method. Polymers H40-P(Asp-AED-ICA)-PEG-OCH$_3$/Cy5 and H40-P(Asp-AED-ICA)-PEG-OCH$_3$/Cy5/GE11 were only used for the cellular uptake analysis. For all other experiments, H40-P(Asp-AED-ICA)-PEG-OCH$_3$ and H40-P(Asp-AED-ICA)-PEG-OCH$_3$/GE11 were used.

Preparation of siRNA-Complexed Unimolecular NPs (i.e., siRNA-complexed NPs) and Gel Retardation Assay. To prepare siRNA-complexed NPs, siRNA and H40-P(Asp-AED-ICA)-PEG were dissolved in PBS and the solution was mixed for 30 min under gentle shaking. The binding ability of siRNA to NPs was studied by agarose gel electrophoresis. The siRNA-complexed NPs were prepared at different N/P ratios (molar ratio of nitrogen in polymers to phosphorus in siRNA: 2, 5, 7, 10, and 15). Electrophoresis was carried out on 1% agarose gel in a TAE (Tris-acetate-EDTA) buffer solution with a current of 100 V for 35 min. The final siRNA concentration was 1 µg per well. The retardation of the complexes was visualized on a UV illuminator (Bio-Rad Baloratories, Inc., Hercules, Calif., USA) to show the position of the complexed siRNA band relative to that of naked siRNA.

Characterization. $^1$H NMR spectra of all intermediate and final polymer products were recorded on a Varian Mercury Plus 300 spectrometer in DMSO-d$_6$ or CDCl$_3$ at 25° C. Molecular weights (M$_n$ and M$_w$) and polydispersity indices (PDI) of the polymers were determined by a gel permeation chromatography (GPC) system equipped with a refractive index detector, a viscometer detector, and a light scattering detector (Viscotek, USA). Fourier transform infrared (FT-IR) spectra were recorded on a Bruker Tensor 27 FT-IR spectrometer. The morphologies of the siRNA-complexed NPs were studied by dynamic light scattering (DLS; Zeta-Sizer Nano ZS90, Malvern Instruments, USA; 0.5 mg/mL) and transmission electron microscopy (TEM, FEI Tecnai G$^2$ F30 TWIN 300 KV, E.A. Fischione Instruments, Inc. USA).

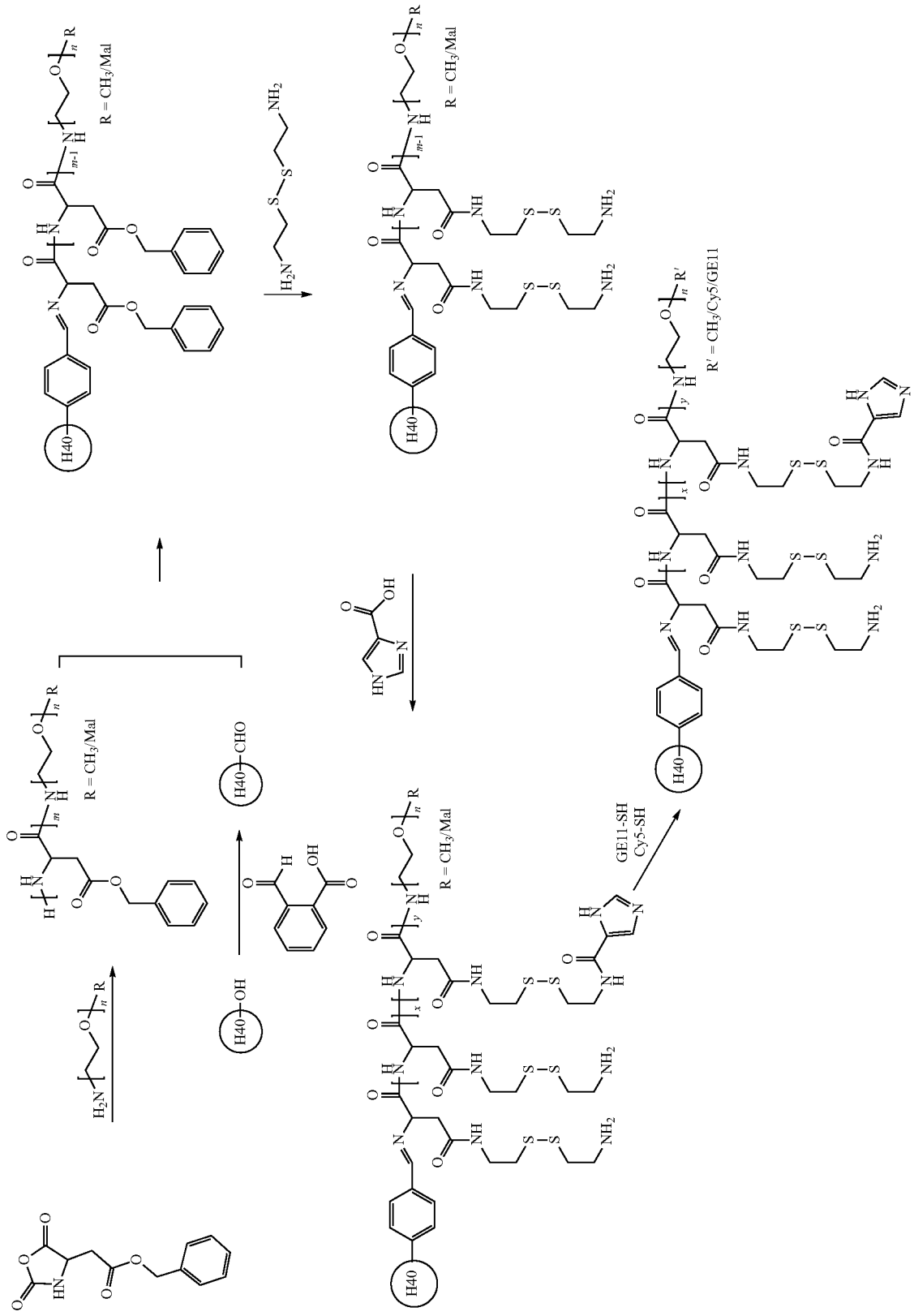

Scheme 1. A Synthetic Scheme of Multi-Arm Star Block Copolymer H40-P(Asp-AED-ICA)-PEG-OCH$_3$/Cy5/GE11.

Results and Discussion

Figure 2A:
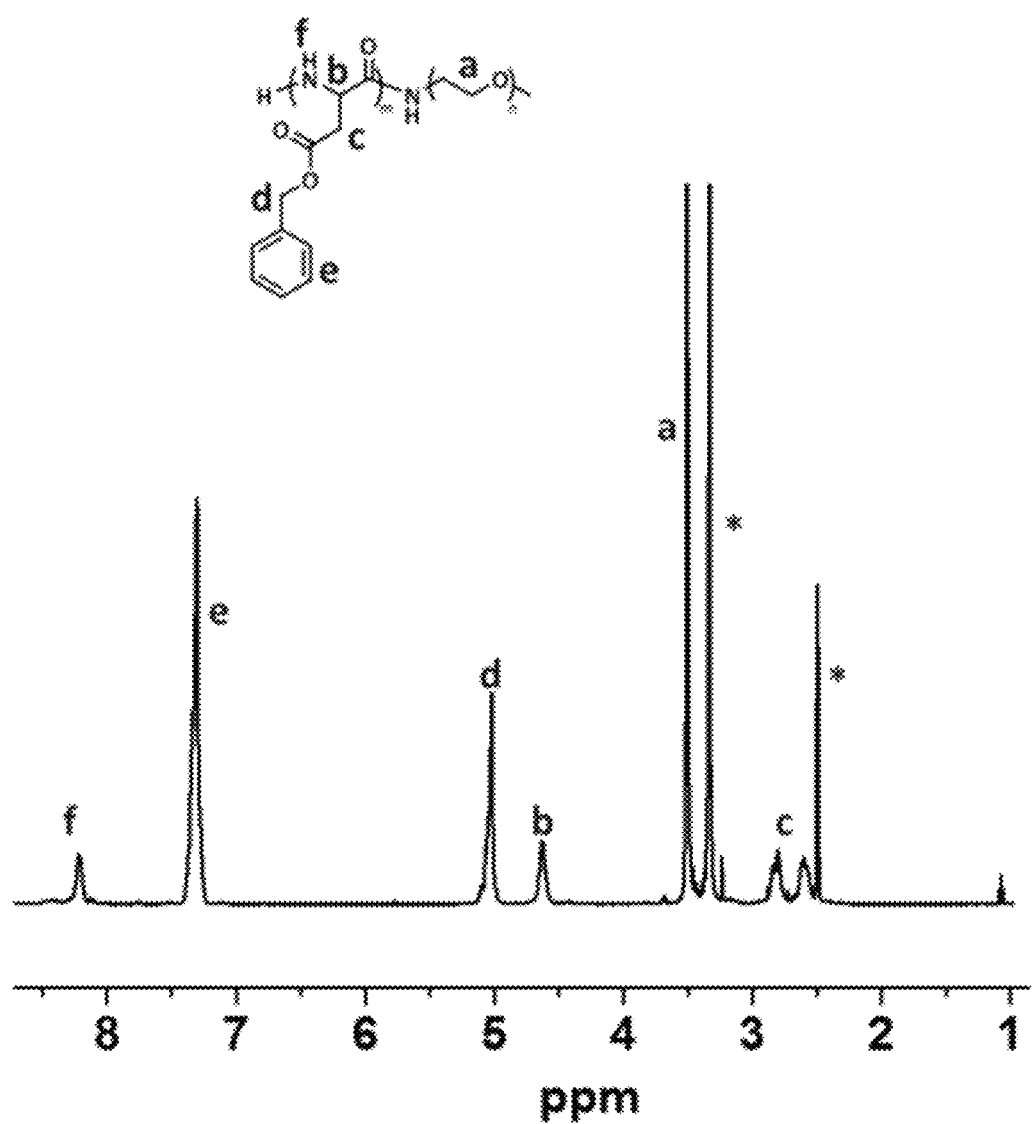
FIGS. 2A-2C show $^1$H NMR spectra of P(BLA-NCA)-PEG-OCH$_3$ (FIG. 2A), P(BLA-NCA)-PEG-Mal (FIG. 2B), and H40-CHO (FIG. 2C).
Figure 2B:
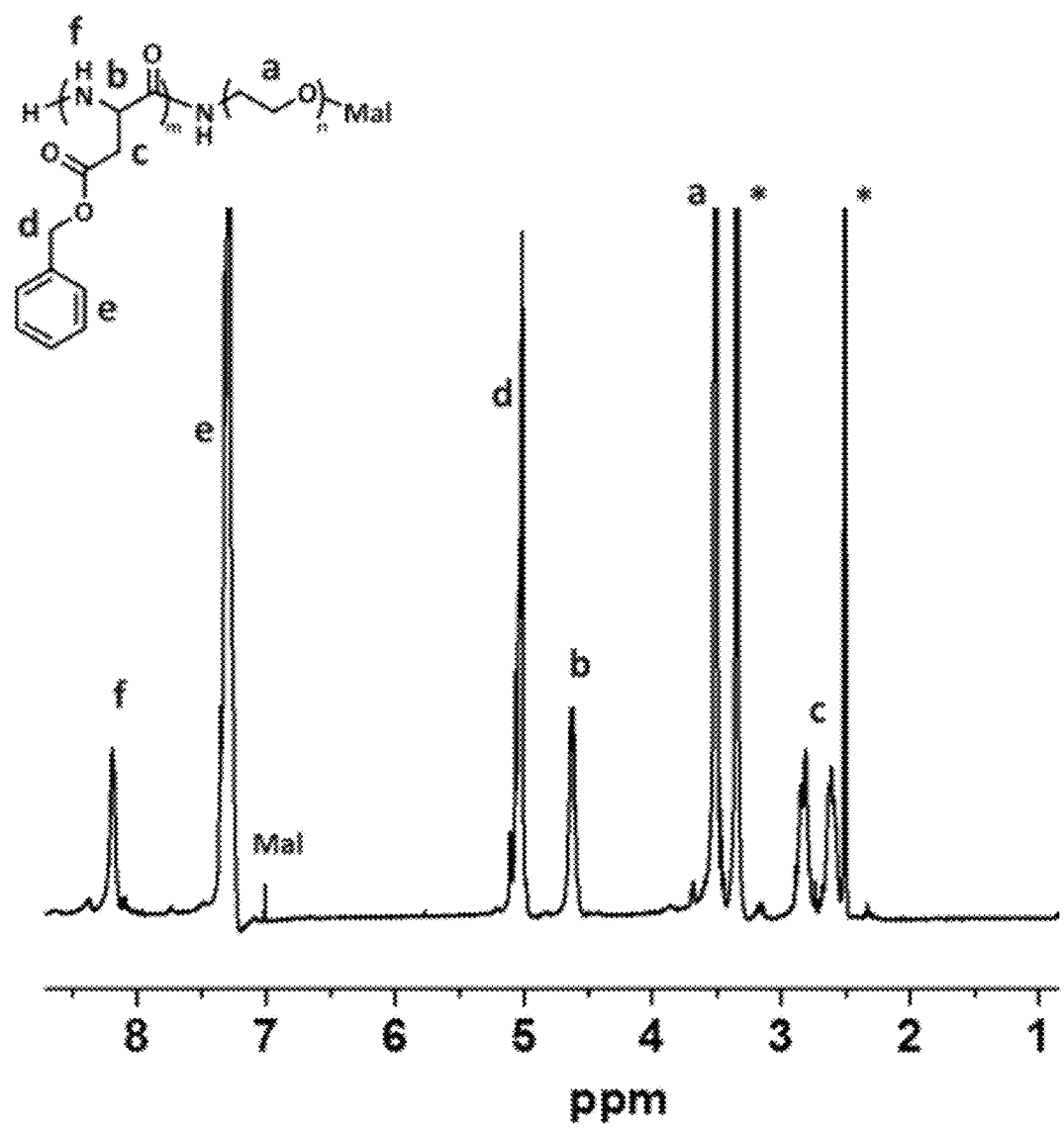

Polymer Synthesis and siRNA Encapsulation. pH/redox dual-sensitive multi-arm star block copolymer H40-P(Asp-AED-ICA)-PEG-OCH$_3$/Cy5/GE11 was synthesized as outlined in Scheme 1. P(BLA-NCA)-PEG-OCH$_3$ and P(BLA-NCA)-PEG-Mal were first synthesized by ring-opening polymerization of BLA-NCA using NH$_2$-PEG-OCH$_3$ and NH$_2$-PEG-Mal as the macro-initiators, respectively. Their chemical structures were confirmed by $^1$H NMR spectra as shown in FIGS. 2(A) and (B). The peaks at (e) 7.28-7.40 ppm and (d) 5.15 ppm were assigned to the protons in the benzyl and methylene groups in the P(BLA-NCA) side chains, respectively. The signals labeled as (c) at 2.6-2.8 ppm were ascribed to the methylene group of the side chain that connects the main chain in the P(BLA-NCA) segment. The peak located at (a) 3.57 ppm corresponded to the methylene protons of the oxyethylene repeat units in the PEG segment. The Mal group in the P(BLA-NCA)-PEG-Mal at 6.7 ppm was also observed. The number of BLA-NCA repeat units in the polymers was calculated to be 20 based on the relative intensity ratio of the methylene proton (a) of the PEG chain and the methylene proton (d) near the benzyl group of the PBLA chain. The molecular weights of the NH$_2$-PEG-OCH$_3$ and NH$_2$-PEG-Mal polymers as measured by GPC (Table 1) were 9,040 and 9,105 g/mol, respectively, which was consistent with that determined by the $^1$H NMR analyses.

Figure 2C:
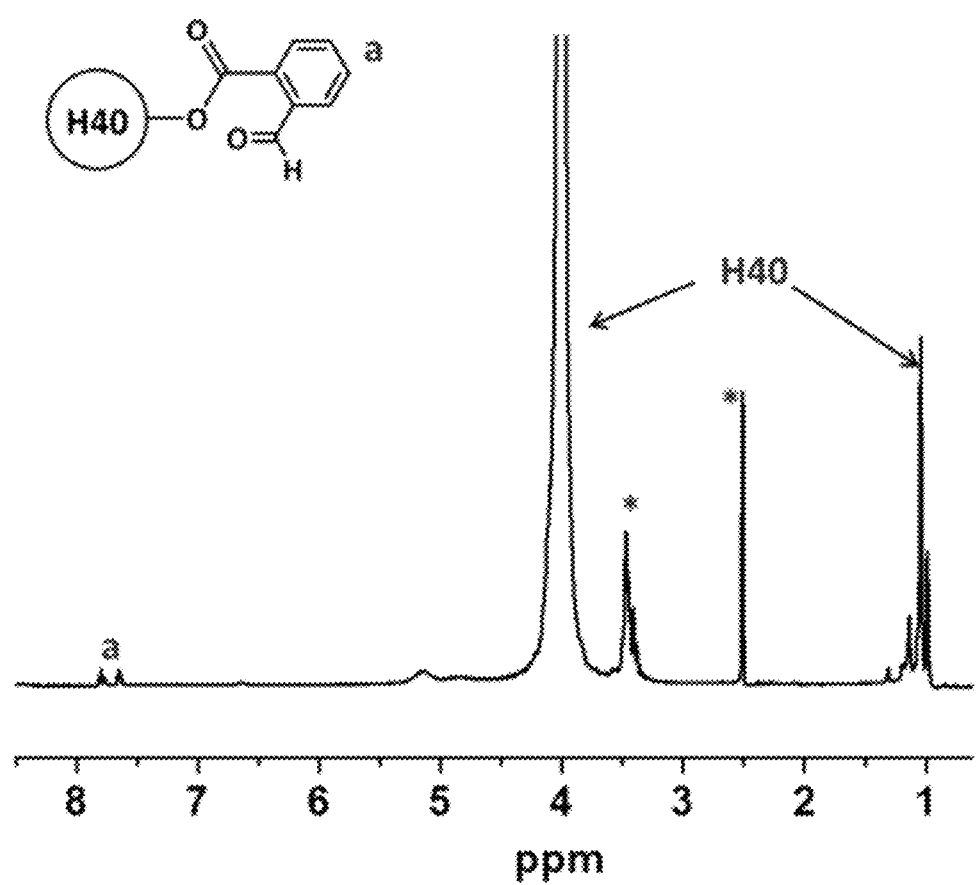
Figure 3A:
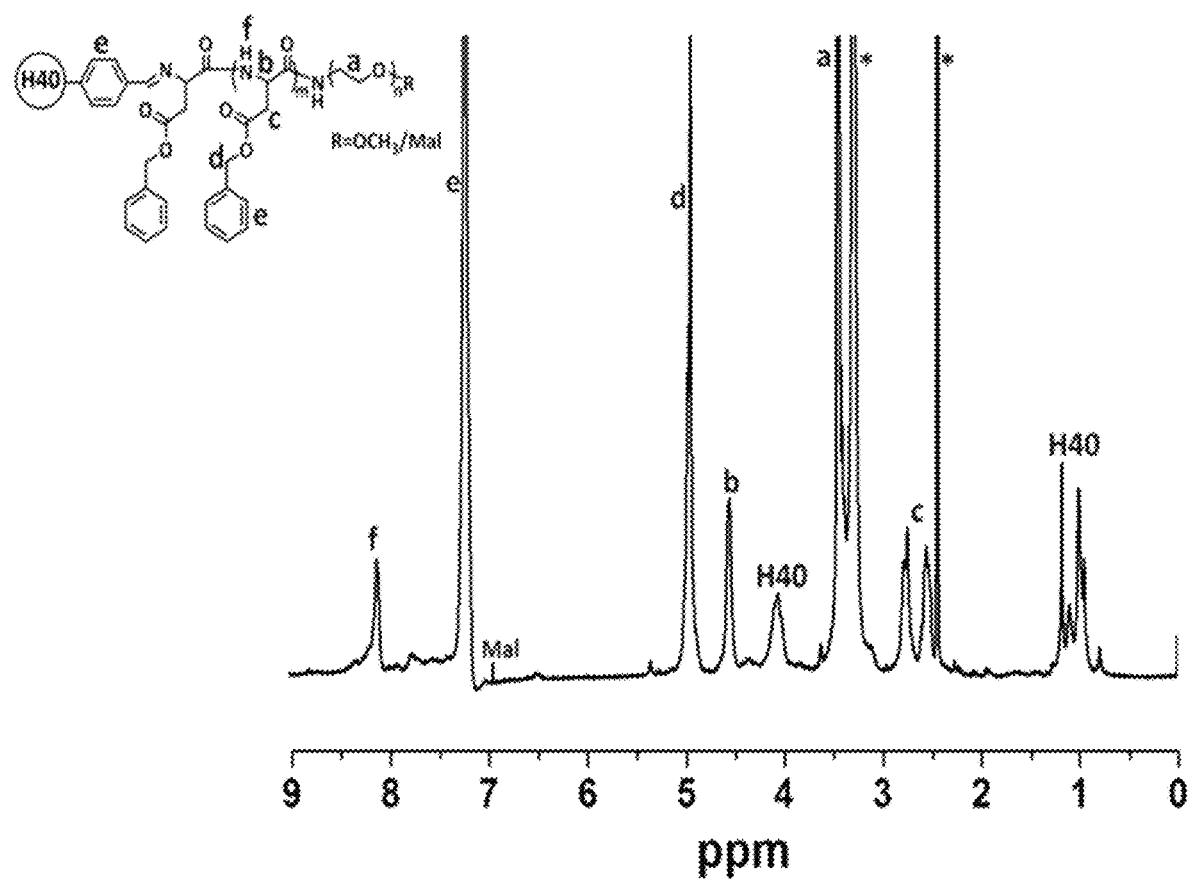
FIGS. 3A-3D show $^1$H NMR spectra of H40-P(BLA-NCA)-PEG-OCH$_3$/Mal (FIG. 3A), H40-P(Asp-AED)-PEG-OCH$_3$/Mal (FIG. 3B), H40-P(Asp-AED-ICA)-PEG-OCH$_3$/Mal (FIG. 3C), and H40-P(Asp-AED-ICA)-PEG-OCH$_3$/Cy5/GE11 (FIG. 3D).
Figure 3B:
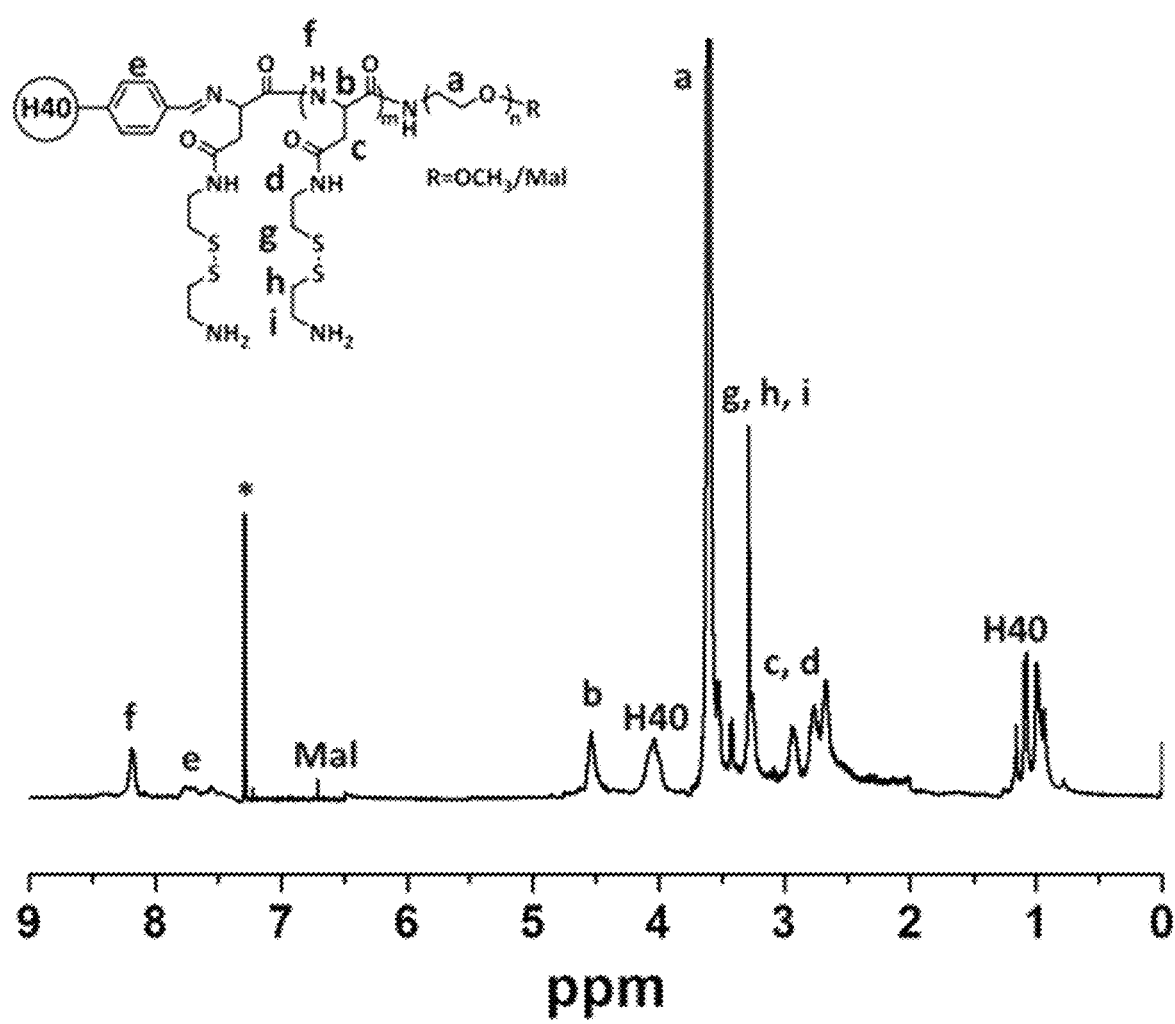
Figure 3C:
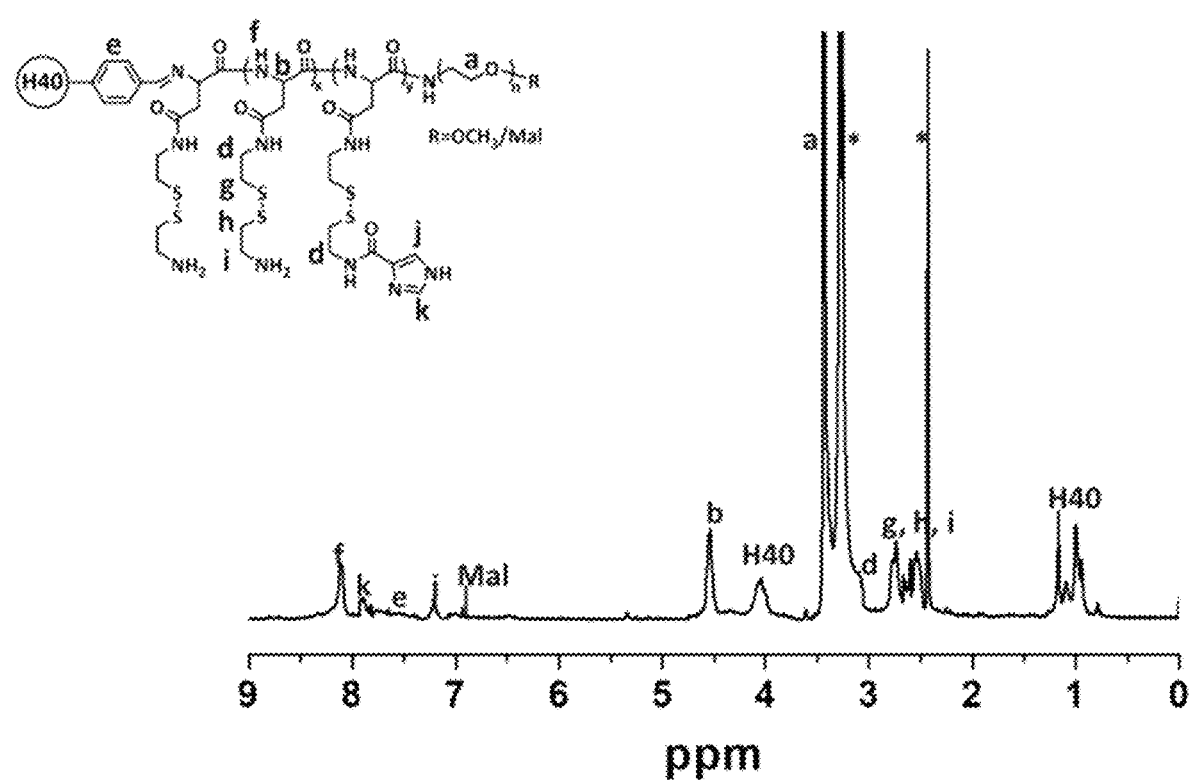

The benzylaldehyde-functionalized H40 (H40-CHO) was prepared by an esterification reaction. The chemical structure was also confirmed by $^1$H NMR spectrum (FIG. 2C). The peaks at 0.97-1.2 ppm and 3.8-4.1 ppm were assigned to the protons in H40. The peaks at (a) 7.6-7.8 ppm corresponded to the protons in the phenyl group of H40-CHO as labeled. Thereafter, P(BLA-NCA)-PEG-OCH$_3$ and P(BLA-NCA)-PEG-Mal (molar ratio: 3.1/1) polymers were then conjugated to H40-CHO through imine bonds to form H40-P(BLA-NCA)-PEG-OCH$_3$/Mal. In the $^1$H NMR spectrum shown in FIG. 3(A), other than the proton peaks assigned to P(BLA-NCA)-PEG-OCH$_3$ and P(BLA-NCA)-PEG-Mal, proton peaks ascribed to H40 were also observed. The GPC analyses further demonstrated the formation of H40-P(BLA-NCA)-PEG-OCH$_3$/Mal and its molecular weight was measured to be 200,833 Da, which was significantly larger than that of the linear NH$_2$-PEG-OCH$_3$ or NH$_2$-PEG-Mal polymers. The average number of arms in the H40-P(BLA-NCA)-PEG-OCH$_3$/Mal was calculated to be 22 based on the molecular weights of H40-P(BLA-NCA)-PEG-OCH$_3$/Mal, NH$_2$-PEG-OCH$_3$, and NH$_2$-PEG-Mal. Thereafter, the H40-P(BLA-NCA)-PEG-OCH$_3$/Mal polymer underwent aminolysis by using 2-aminoethyl disulfide (AED) to form water-soluble polymer H40-P(Asp-AED)-PEG-OCH$_3$/Mal. As shown in FIG. 3(B), the absence of proton peaks at 7.28-7.40 ppm and 5.15 ppm, and the presence of proton peaks at 2.71 and 3.17 ppm ascribed to the protons in AED, demonstrated the formation of H40-P(Asp-AED)-PEG-OCH$_3$/Mal.

Figure 3D:
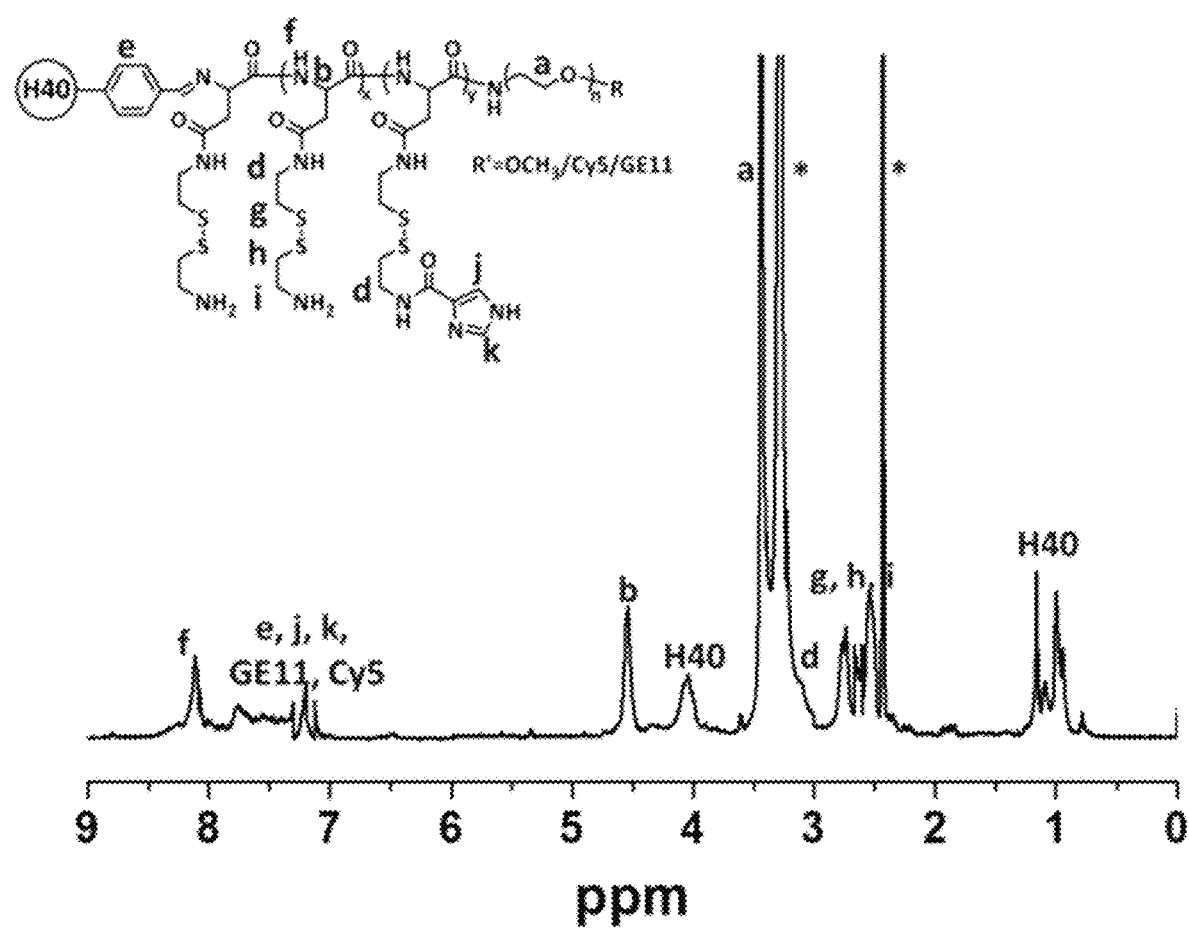

Imidazole groups were selectively conjugated to H40-P(Asp-AED)-PEG-OCH$_3$/Mal (molar ratio: 5/1) through an amidization reaction for enhanced endosomal/lysosomal escape. The characteristic proton peaks at (j) 7.23 and (k) 7.91 ppm for imidazole groups were observed in FIG. 3 (C). In the last step, GE11 peptide and Cy5 dye were conjugated to H40-P(Asp-AED-ICA)-PEG-OCH$_3$/Mal (molar ratio: 3/2/1) though a Mal-SH reaction. Proton peaks assigned to the GE11 and Cy5 molecules, as labeled in FIG. 3(D), were also observed.

TABLE 1

GPC analyses of polymers.

| Polymers | $M_n$ (g/mol) | PDI |
|---|---|---|
| P(BLA—NCA)—PEG—OCH$_3$ | 9,040 | 1.4 |
| P(BLA—NCA)—PEG—Mal | 9,105 | 1.3 |
| H40—P(BLA—NCA)—PEG—OCH$_3$/Mal | 200,833 | 1.6 |
| H40—P(Asp-AED)—PEG—OCH$_3$/Mal | 186,406 | 1.7 |
| H40—P(Asp-AED—ICA)—PEG—OCH$_3$/Mal | 187,130 | 1.6 |

Figure 4A:
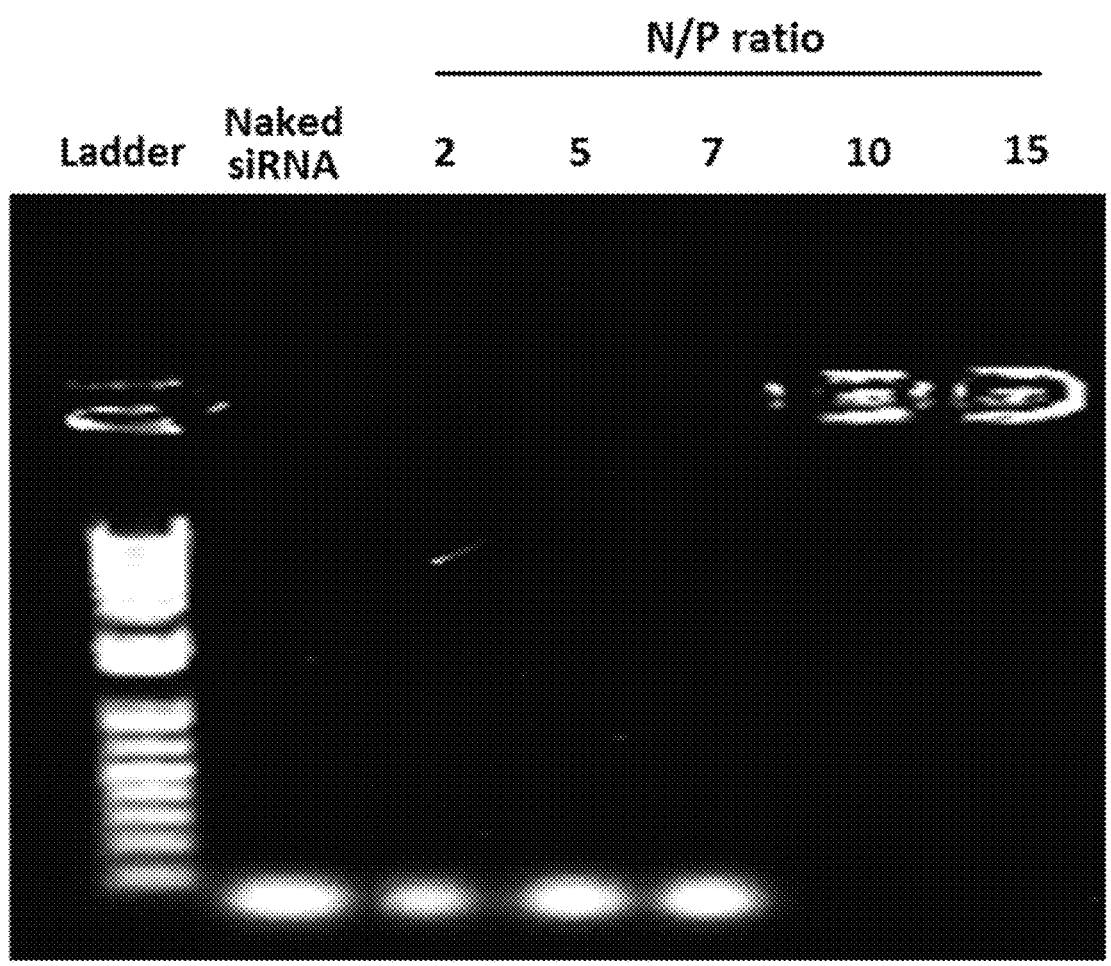
FIG. 4A shows gel retardation assays of siRNA/NPs with various N/P ratios.
Figure 4B:
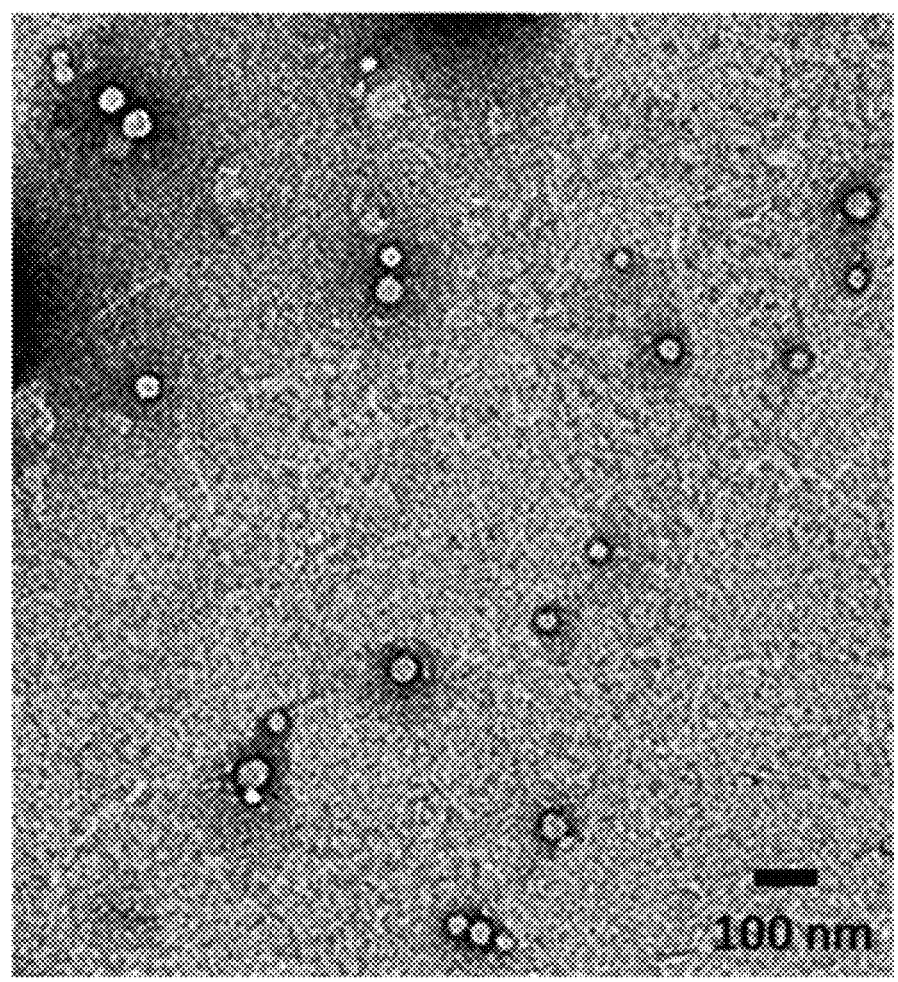
FIG. 4B shows transmission electron microscopy (TEM) images of the siRNA-complexed NPs (N/P=10).

The cationic polymer H40-P(Asp-AED-ICA)-PEG, which had good solubility in aqueous solutions, was able to form the unimolecular NPs. Because of its covalent nature, the unimolecular NPs had excellent stability in vitro and in vivo. siRNA (GFP-siRNA was used as a model siRNA) was electrostatically complexed with the cationic P(Asp-AED-ICA) polymer to form siRNA-complexed NPs. The complexation was evaluated using agarose gel electrophoresis. As shown in FIG. 4 (A), siRNA-complexed NPs with various N/P ratios were tested and siRNA lost mobility in the electric field when the N/P ratio reached 10, which was selected for the following tests. The siRNA loading level, defined by the weight percentage of the siRNA in the siRNA-complexed NP was 16.3% at N/P ratio of 10, and the loading efficiency is 100%. The average hydrodynamic diameter of the siRNA-complexed NPs was 68.3 nm (PDI=0.14) as measured by dynamic light scattering (DLS). Transmission electron microscopy (TEM) observation showed that the siRNA-complexed NPs were uniform, with an average size of around 39 nm (FIG. 4 (B)).

Example 2: In Vitro Analyses

In Vitro siRNA Release. The release profiles of siRNA from siRNA-complexed NPs were studied in a glass apparatus at 37° C. in a release medium at four conditions: (1) pH 7.4, (2) pH 5.3, (3) pH 7.4+10 mM GSH, and (4) pH 5.3+10 mM GSH. siRNA-complexed NP solutions (5 mL; 100 µg/mL) were enclosed in a dialysis bag. The dialysis bag was immersed in 50 ml of the release medium and kept at 37° C. under a horizontal laboratory shaker (Thermo Scientific MaxQ Shaker, USA) at 100 rpm. At specific time points, 3 ml of release media were collected and replaced by the same volume of fresh media. GFP-siRNA-Cy5.5 was used in this experiment. The amount of released siRNA was analyzed based on the UV-vis intensity of Cy5.5 at 649 nm.

Cellular Uptake. The cellular uptake behaviors of the NPs in MDA-MB-468 TNBC cell lines were analyzed using a fluorescence microscope based on the Cy5 dye conjugated on the NPs. Cells were seeded (1×10$^5$ cells/ml) onto 8-well high-optical-quality plates and grown overnight. Cells were treated with either non-targeted NPs, targeted NPs, or targeted NPs with free GE11 peptide (2 µM; blocking assay) at an NP concentration of 100 µg/ml. After 2 h incubation, cells were washed with PBS twice, fixed with 4% PFA, and stained with DAPI for 4 h. Then the cells were mounted with Prolong Gold anti-fade reagent. The cellular uptake was observed using a fluorescence microscope (Nikon, Melville, N.Y.). Digital monochromatic images were acquired using NIS-Elements BR Software.

Endosomal/Lysosomal Escape. To assess the endosomal/lysosomal escape behaviors of the NPs, MDA-MB-468 cells were incubated with siRNA-complexed NPs for 2 h at 37° C. Cells treated with pure medium or free siRNA were used as negative controls. The siRNA labeled with Cy5.5 was used for intracellular tracking. The cells were washed three times with PBS, followed by staining with LysoTracker Green DND-26 (100 nM) for endosomes/lysosomes and Hoechst (5 ng/mL) for the nuclei, for 20 min at 37° C. Cells were then washed three times with PBS. The cellular localization of siRNA was visualized with a fluorescence microscope (Nikon, Melville, N.Y.).

In Vitro siRNA Transfection. Cellular transfection was performed on GFP-expressing MDA-MB-468 TNBC cells using flow cytometry and a fluorescence microscopy. GFP-expressing MDA-MB-468 cells were provided by Professor Wei Xu. For the flow cytometry assay, cells were seeded at a density of 50,000 cells/well on a 24-well plate and incubated overnight. Cells were treated with pure medium (control), siRNA-complexed non-targeted NPs (siRNA-NT), siRNA-complexed targeted NPs (siRNA-T), and siRNA complexed with RNAiMAX (i.e., siRNA-RNAiMAX; positive control). The concentration of siRNA was 40 nM. After 24 h incubation, cells were washed twice with PBS and harvested with 0.25% trypsin. Cells were collected by centrifugation at 200 g for 5 min, washed twice with PBS, fixed with paraformaldehyde (PFA) for 15 min, and resuspended in 500 µL PBS for analysis. The transfection efficiency was examined by quantifying GFP expression levels in the cells using an Accuri™ C6 flow cytometry system (BD Biosciences, USA). A minimum of 10,000 cells was analyzed from each sample.

For fluorescence microscope imaging, cells were seeded (50,000 cells/well) in an 8-well chamber slide system. Cells were treated with the same five groups as described above. After 24 h incubation, cells were washed twice with PBS, fixed with PFA for 15 min, stained with DAPI for 4 h, and mounted with ProLong Gold Antifade Mountant. Images were acquired with a fluorescence microscope (Nikon, Melville, N.Y.) to observe the GFP expression levels in the cells. Digital monochromatic images were acquired using NIS-Elements BR Software.

Cell Viability Assays. Cell viability tests were conducted using the 3-[4,5-dimethylthiazol-2-yl]-2,5-diphenyltetrazolium bromide (MTT) assay. To test the cytotoxicity of the pure (empty) NPs, MDA-MB-468 cells were seeded in quadruplicate on 96-well plates and incubated overnight. Cells were treated with NPs at different concentrations (i.e., 10, 20, 50, 100, and 500 µg/mL). Cells treated with pure medium were used as the control group. After 24 h of incubation, a standard MTT assay was performed by aspirating the treatment media, adding 25 lit of the medium containing 0.5 mg/ml MTT agent, and incubating at 37° C. for 4 h. Thereafter, the medium was aspirated and 75 µL of DMSO was added to each well. The plates were then measured at 570 nm using a spectrophotometer (Quant, Bio-Tek Instruments, Winooski, Vt.), and the average absorbance and percent of cell viability relative to the control (pure medium) were calculated. The cytotoxicity of siRNA-complexed NP systems was also studied. Similarly, cells were treated with pure medium (control), siRNA-NT, siRNA-T, siRNA-RNAiMAX, and RNAiMAX at the equivalent amount of siRNA (40 nM). After 24 h of incubation, the aforementioned MTT protocol was performed and the cell viabilities relative to the control (pure medium) were calculated.

Figure 4C:
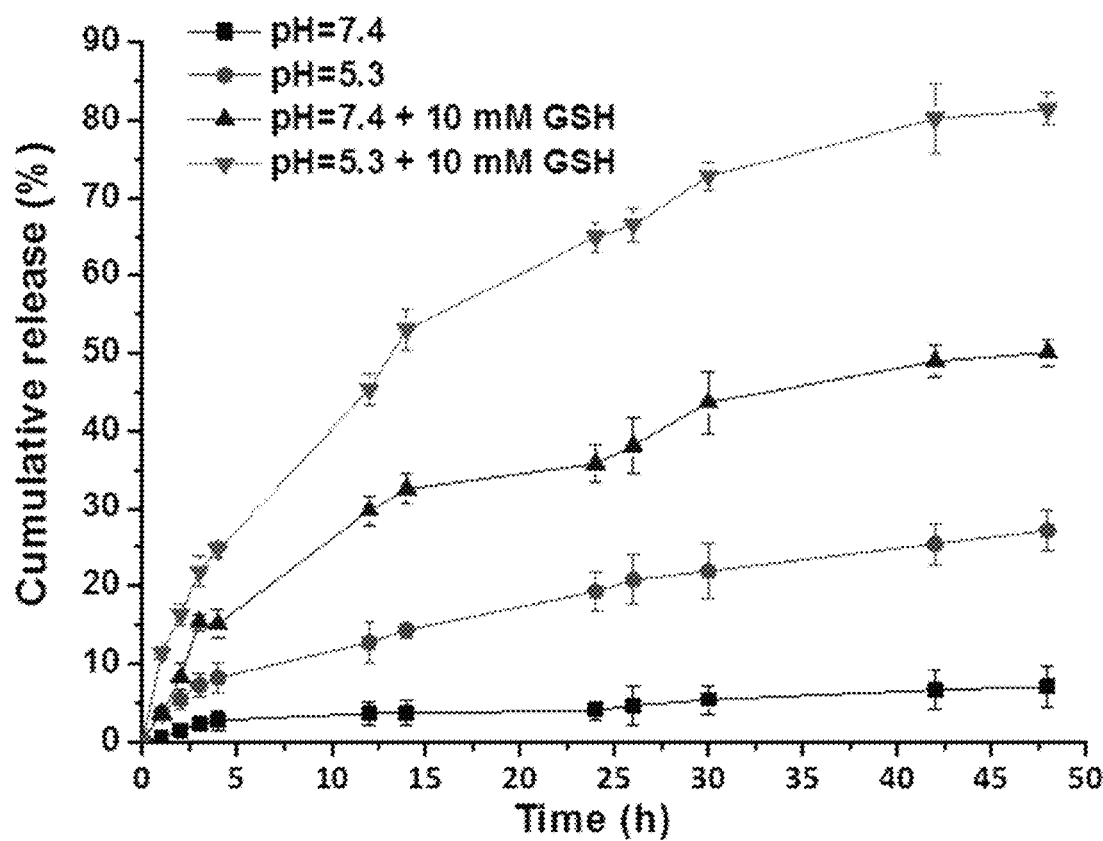
FIG. 4C shows in vitro siRNA release from siRNA-complexed NPs in different buffers at 37° C. Data represent mean±SD (n=3).

Results and Discussion.

pH/redox Dual-Sensitive siRNA Release. NPs with pH/redox dual-sensitive structures were designed to achieve decomplexation of siRNA from cationic nanocarriers and controlled release of siRNA to enhance gene silencing efficiency. To verify the pH/redox dual-sensitive release behavior, in vitro release analyses were conducted by monitoring Cy5.5-labeled siRNA. As shown in FIG. 4(C), the release rate was very slow at neutral pH (7.4) without adding GSH, with 7.1% of siRNA released after 48 h. In comparison, the addition of GSH (10 mM) to the solution resulted in an increased siRNA release rate (50.1% of siRNA released after 48 h). Meanwhile, 27.2% of siRNA was released at a pH of 5.3 after 48 h, which is much faster compared to that at a neutral pH. Moreover, dual stimuli (pH 5.3 and 10 mM GSH) led to the quickest siRNA release (81.4% of siRNA released after 48 h). Taken together, these observations suggest that siRNA can be decomplexed from siRNA-complexed NPs inside of cells.

Figure 5:
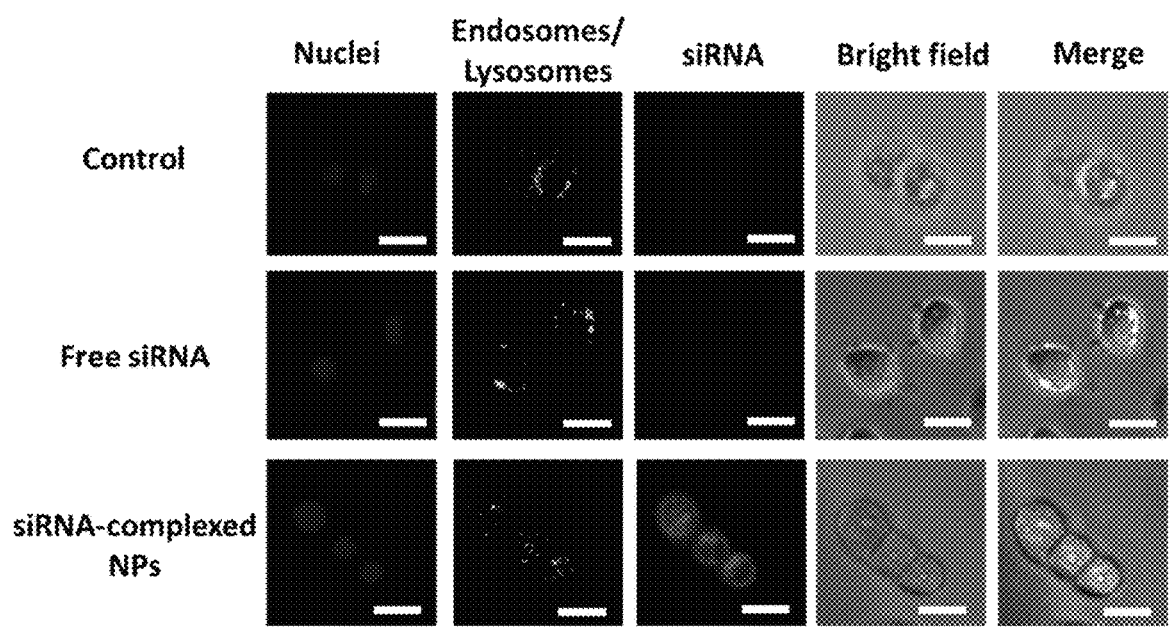
FIG. 5 shows an assessment of the endosomal/lysosomal escape of siRNA-complexed NPs in MDA-MB-468 cells after 2 h incubation. Endosomes/lysosomes stained with Lysotracker. siRNA was labeled with Cy5.5. The nuclei were stained with Hoechst. Scale bar: 20 μm.
Figure 6:
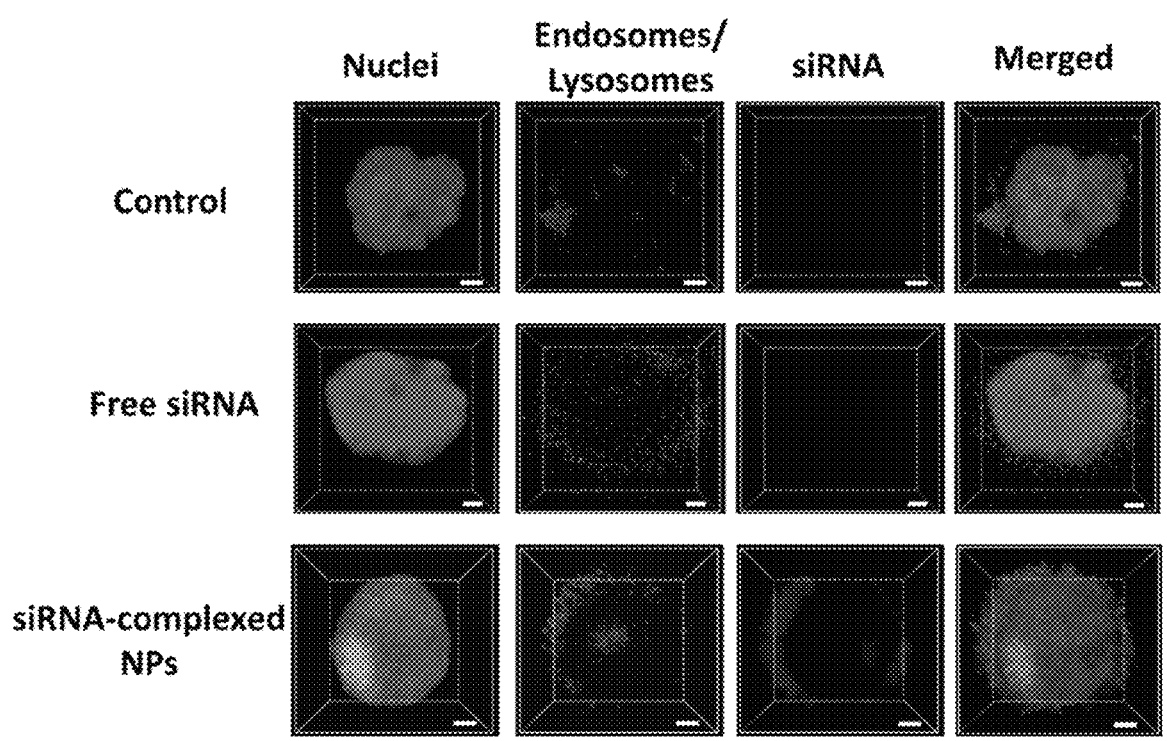
FIG. 6 shows z-stack images for the assessment of the endosomal/lysosomal escape of siRNA-complexed NPs in MDA-MB-468 cells. Scale bar: 2 μm.

Enhanced Endosomal/Lysosomal Escape Capability of NPs. Another major obstacle in designing nanocarriers for siRNA delivery is their poor endosomal/lysosomal escape capabilities. siRNA needs to be released into the cytoplasm for efficient gene silencing. Therefore, the siRNA nanocarriers were functionalized with endosomal/lysosomal escape capabilities. As mentioned above, the imidazole groups in the cationic segment promote endosomal/lysosomal escape through the proton-sponge effect, thereby facilitating the release of siRNA to the cytosol. To verify endosomal/lysosomal escape, fluorescence microscopy was used to assess the intracellular localizations of siRNA. The cells (MDA-MB-468 TNBC cell line) were treated with pure medium (control) or media containing free siRNA or siRNA-complexed nanoparticles. siRNA was labeled with Cy5.5 for detection. After 2 h incubation, the nucleus and endosomes/lysosomes of cells were stained with Hoechst and Lysotracker, respectively. As shown in FIG. 5, siRNA complexed with NPs were taken up efficiently as signified by the strong Cy5.5 signal. The Cy5.5 signals barely overlapped with the Lysotracker signals (endosomes/lysosomes), and they were distributed relatively uniformly in the cytosol, demonstrating that the majority of the siRNA escaped from the endosomes/lysosomes. The z-stack images shown in FIG. 6 also confirmed the excellent endosomsomal/lysosomal escape capabilities of the siRNA-complexed NPs. NPs capable of effective endosomal/lysosomal escape should lead to efficient gene silencing.

Figure 7:
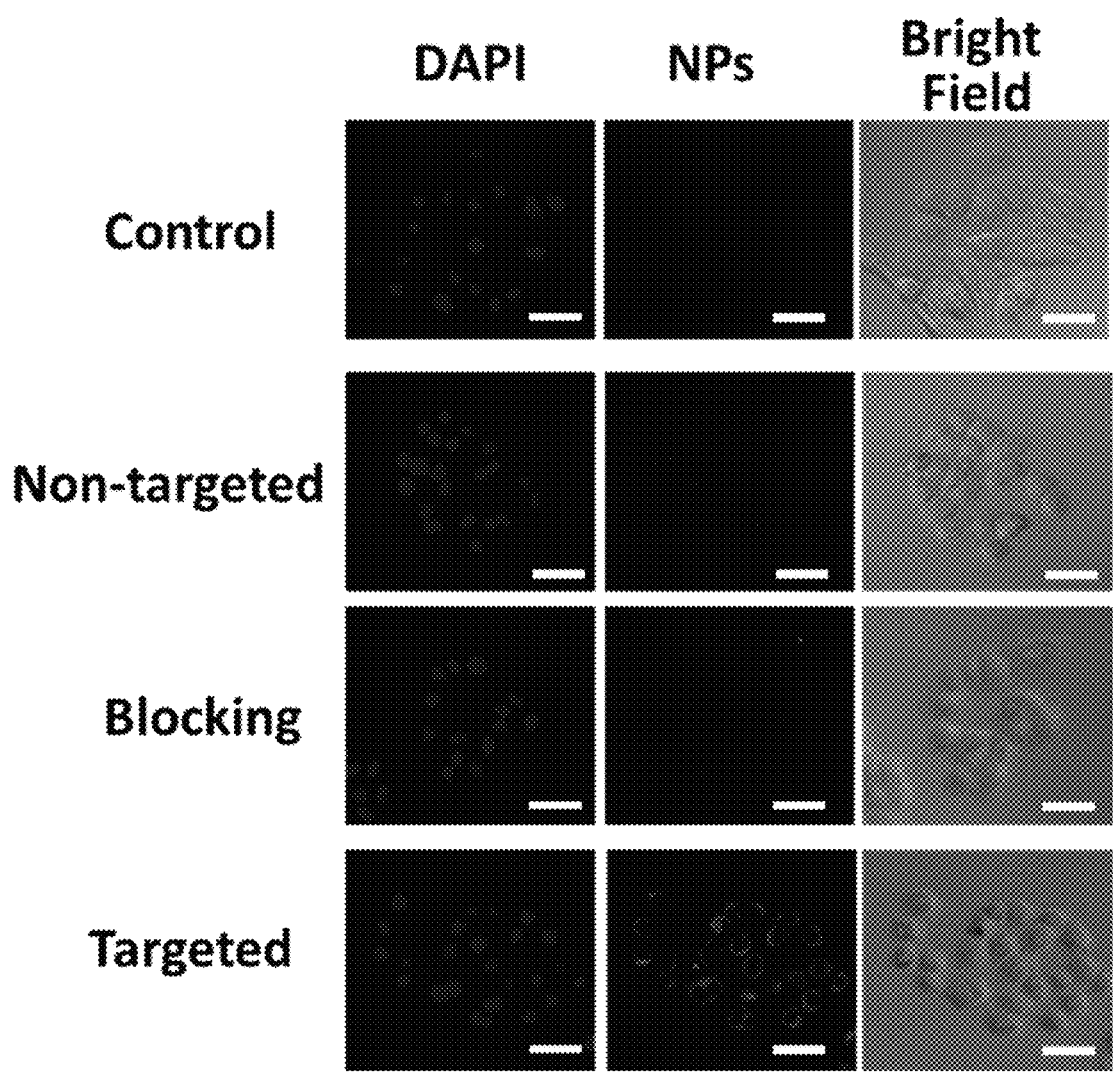
FIG. 7 shows the in vitro cellular uptake analysis. Fluorescence images of MDA-MB-468 TNBC cells incubated with pure medium (control), Cy5-labeled non-targeted (without GE11 conjugation) NPs, Cy5-labeled targeted (GE11-conjugated) NPs with a blocking dose (2 μM) of GE11 (i.e., blocking), and Cy5-labeled targeted NPs at 37° C. for 2 h (NP concentration: 100 μg/mL). Targeted NPs significantly enhanced the cellular uptake in EGFR-overexpressing TNBC cells. Scale bar: 50 μm.

In Vitro Cellular Uptake. EGFR is overexpressed in many common types of cancer. Here, an EGFR targeting peptide, GE11, was used as an active-tumor-targeting ligand to enhance cellular uptake. MDA-MB-468, a TNBC cell line that overexpresses EGFR, was used as the model cell line. Cells were incubated with either non-targeted (i.e., NPs without GE11 conjugation) or targeted (i.e., GE11 conjugated) NPs for 2 h. Cells without any treatment were used as a negative control. Cy5 was conjugated onto the NPs. Fluorescence imaging analysis was performed to compare cellular uptake. As shown in FIG. 7, the targeted NPs showed a markedly higher Cy5 fluorescence intensity than non-targeted ones. In the blocking experiment (co-incubated cells with free GE11 and targeted NPs), after the EGFR was saturated with free GE11, the cellular uptake of the targeted NPs returned to the level of the non-targeted ones, thereby demonstrating the targeting ability of GE11. Taken together, the targeted NPs increased the cellular uptake of NPs through EGFR-mediated endocytosis.

Figure 8A:
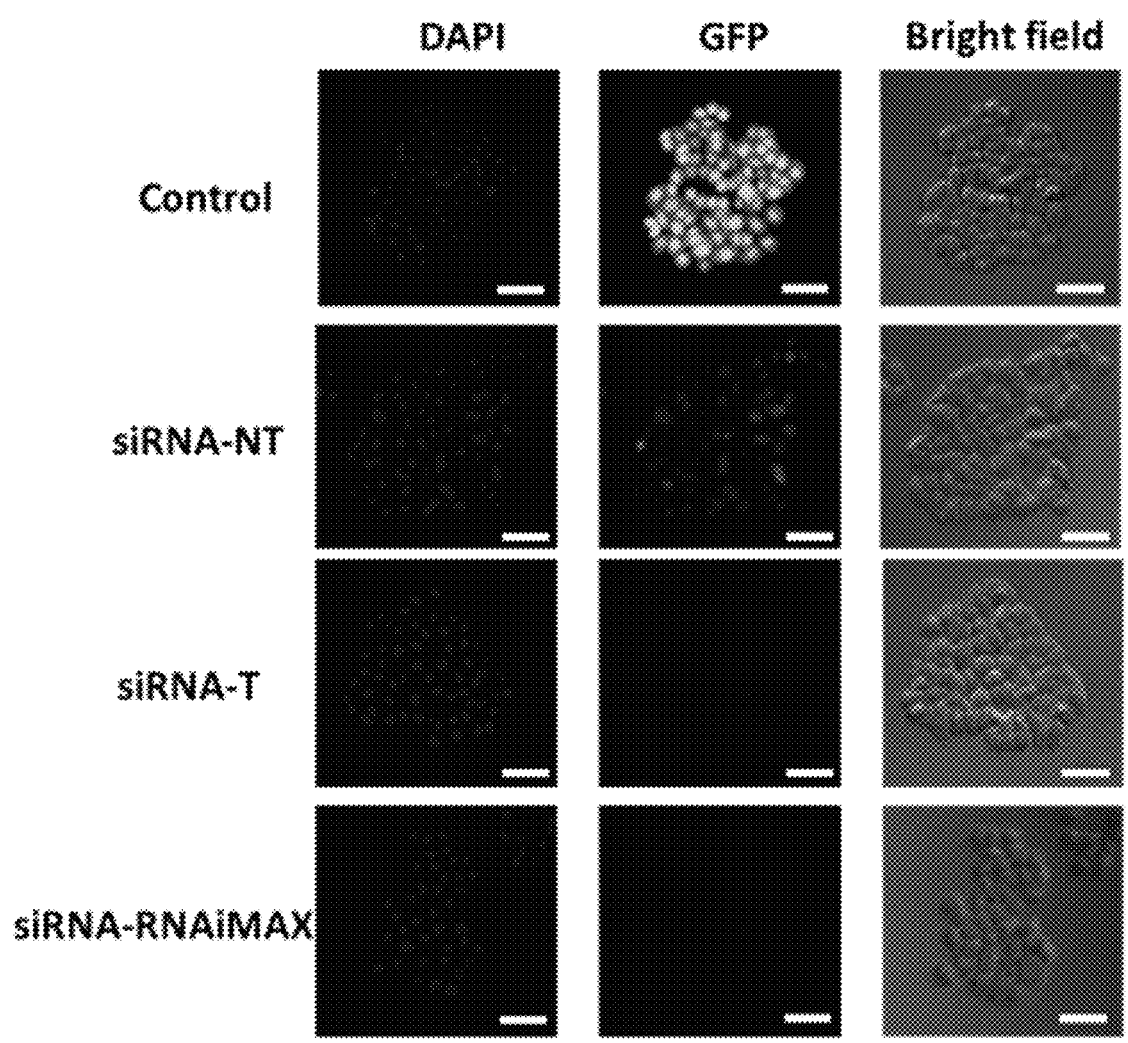
FIGS. 8A-B show an in vitro assessment of gene silencing efficiency using (in FIG. 8A) fluorescence microscope and (in FIG. 8B) flow cytometry. GFP-expressing MDA-MA-468 cells treated with pure medium (control), siRNA-complexed non-targeted NPs (siRNA-NT), siRNA-complexed targeted NPs (siRNA-T), and siRNA-complexed RNAiMAX (siRNA-RNAiMAX) for 24 h (40 nM of GFP-siRNA).
Figure 8B:
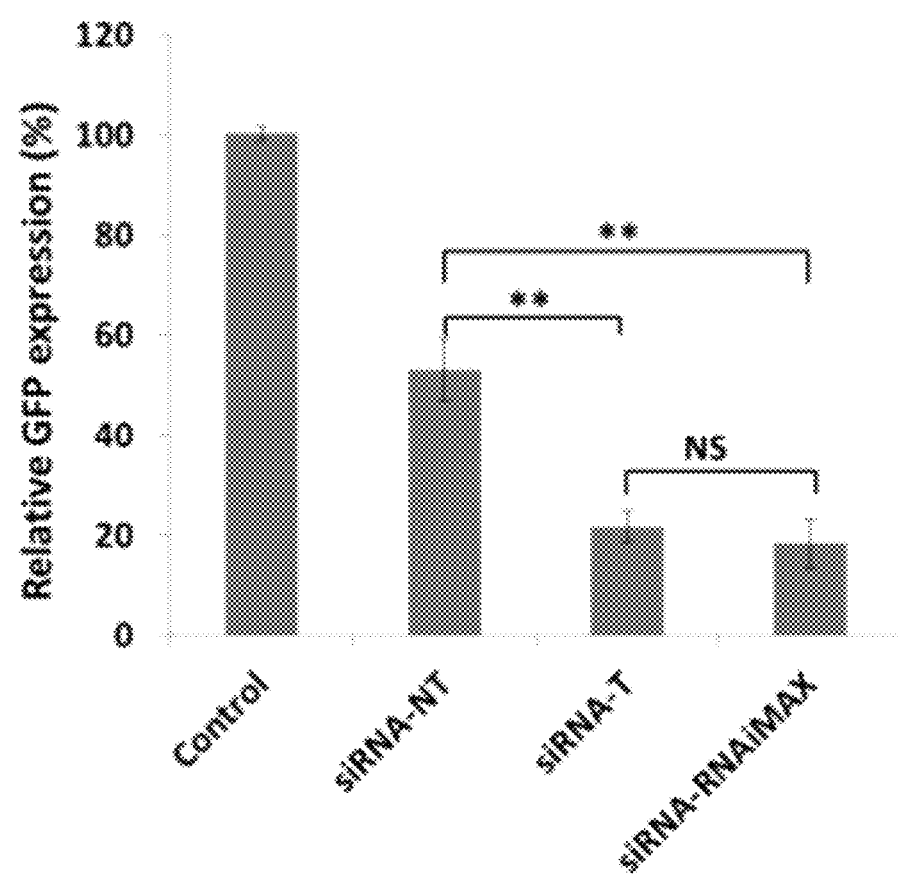
Figure 8C:
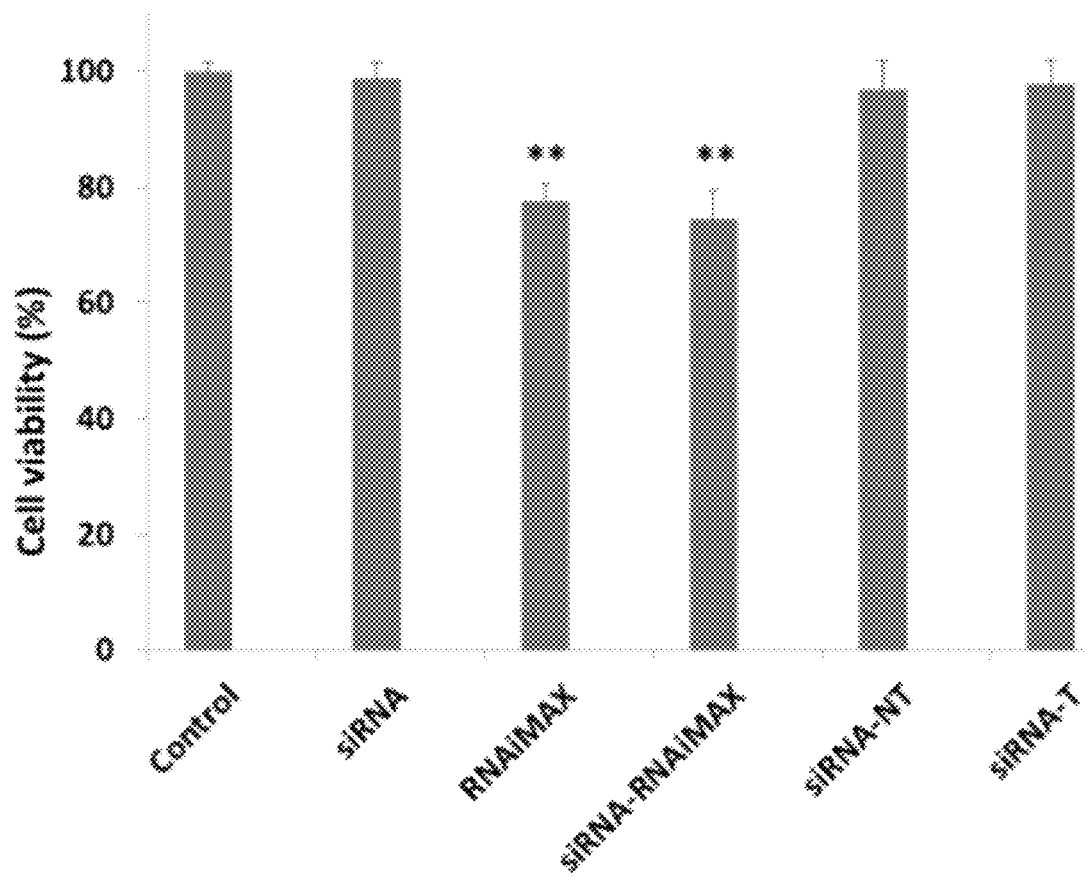
FIG. 8C shows cell viability analysis for MDA-MA-468 cells treated with pure medium (control), siRNA-NT, siRNA-T, siRNA-RNAiMAX, and pure RNAiMAX for 24 h (40 nM of GFP-siRNA). All values are presented as a mean±SD (n=5); **: p<0.01; NS: not significant. Scale bar: 100 μm.
Figure 9:
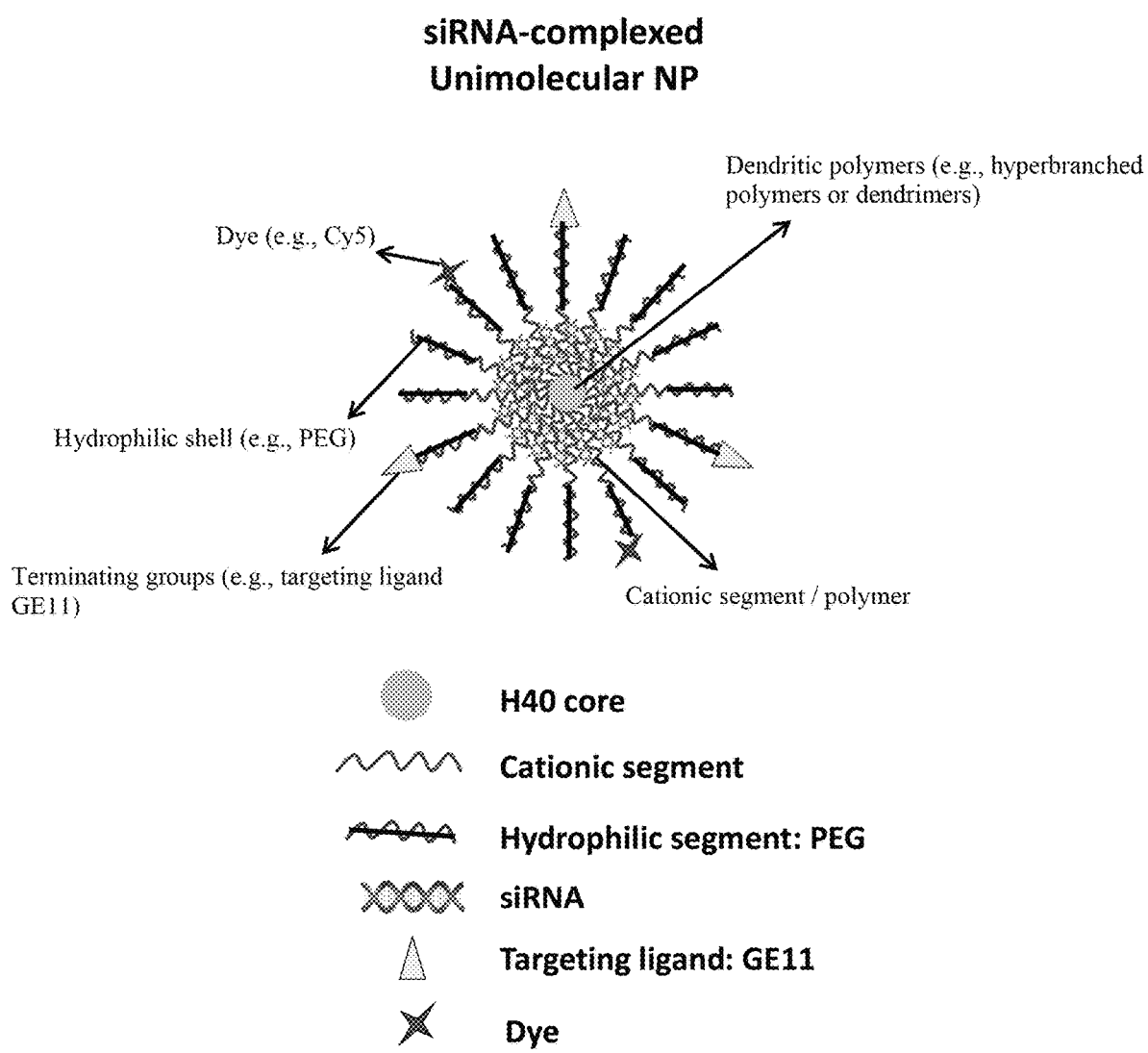
FIG. 9 shows a schematic of an illustrative embodiment of an siRNA-complexed unimolecular nanoparticle (NP) of the present technology including a core comprised of H40 polyester hyperbranched polymer attached to cationic polymers, which in turn are attached to hydrophilic PEG segments and terminating in various functional groups, including dye(s) and the targeting ligand GE11. siRNA molecules partition within the NPs by electrostatic interactions.

In Vitro Gene Silencing Efficiency and Cell Viability Analysis. To determine the potential of NPs to deliver siRNA, gene silencing was assessed in vitro. The gene silencing capacity of GFP-siRNA toward MDA-MB-468 cells stably expressing green fluorescent protein was evaluated for siRNA-complexed non-targeted and targeted NPs. Pure medium was used as the negative control. RNAiMAX, a commercially available transfection agent, was used as the positive control. As shown in FIGS. 8(A) and (B), both targeted and non-targeted groups induced GFP reduction compared to the negative control. As expected based on the cellular uptake analysis, the extent of knockdown was dependent on GE11 functionalization. Relative to the negative control group, the siRNA-complexed non-targeted NPs produced a 47% GFP down-regulation. In contrast, the targeted NPs induced a 79% GFR reduction, which is comparable to that of RNAiMAX treatment (81%). However, the assessment of cell viability on these treatments revealed that siRNA-complexed RNAiMAX exhibited significant cytotoxicity, inducing more than 25% cell death (FIG. 8(C)), which is consistent with the previous report. See N. Segovia, M. Pont, N. Oliva, V. Ramos, S. Borros, N. Artzi, Hydrogel doped with nanoparticles for local sustained release of siRNA in breast cancer, Advanced Healthcare Materials, 4 (2015) 271-280. However, no apparent cytotoxicity associated with NPs was observed. In fact, no significant cytotoxicity was observed for NPs alone up to 500 µg/mL. Taken together, these findings reveal that GE11-conjugated NPs are suitable nanocarriers for siRNA delivery targeted at TNBC cells and, potentially, other EGFR-over-expressing cells.

EQUIVALENTS

While certain embodiments have been illustrated and described, a person with ordinary skill in the art, after reading the foregoing specification, can effect changes, substitutions of equivalents and other types of alterations to the conjugates and nanoparticles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A unimolecular nanoparticle and pharmaceutically acceptable salts thereof, wherein the unimolecular nanoparticle comprises a dendritic polymer core, cationic polymers, and outer poly(ethylene glycol) blocks, wherein the cationic polymers link the dendritic polymer core to the outer poly(ethylene glycol) blocks; and
wherein:
the dendritic polymer core has a molecular weight of about 500 to about 120,000 Da and terminating functional groups selected from the group consisting of-hydroxyl, amino, and carboxylic acid groups;
the cationic polymers are attached to at least 50% of the terminating functional groups of the dendritic polymer core via a pH-sensitive linker, wherein
the pH-sensitive linker comprises an imine, hydrazone, or cis-aconityl group; and
each cationic polymer comprises: a polymeric backbone, cationic functional groups, weakly basic groups, and disulfide bonds,
wherein:
the polymeric backbone is a polyamide and is attached to the cationic functional groups and the weakly basic groups by the disulfide bonds;
the cationic functional groups have a pKa of at least about 8 and are selected from the group consisting of primary amines, secondary amines, tertiary amines, amidines, guanidines, and combinations of two or more thereof;
the molar ratio of the cationic functional groups to the weakly basic groups ranges from 1:1 to 5:1, and
the cationic polymer has a molecular weight from about 1,000 to about 5,000 Da; and
the outer poly(ethylene glycol) blocks are attached to a plurality of the cationic polymers via ester, amide or ether groups and have a terminal group selected from the group consisting of a targeting ligand, OH, O—(C1-C6)alkyl, NH$_2$, biotin, and a dye, wherein the poly(ethylene glycol) block has a molecular weight of about 1,000 to about 15,000 Da.

2. The unimolecular nanoparticle of claim 1, wherein the cationic polymers comprise (C$_2$-C$_6$ alkylene)disulfide(C$_2$-C$_6$ alkyl)amino groups and/or salts thereof, and (C$_2$-C$_6$ alkylene)disulfide(C$_2$-C$_6$ alkyl)aminocarbonylimidazole groups and/or salts thereof.

3. The unimolecular nanoparticle of claim 1, wherein the polymeric backbone is selected from the group consisting of polyasparagine, polyglutamine, polyornithine, and polylysine.

4. The unimolecular nanoparticle of claim 3, wherein the cationic polymers comprise (C$_2$-C$_6$ alkylene)disulfide(C$_2$-C$_6$ alkyl)amino groups and/or salts thereof, and (C$_2$-C$_6$ alkylene)disulfide(C$_2$-C$_6$ alkyl)aminocarbonylimidazole groups and/or salts thereof.

5. The unimolecular nanoparticle of claim 1, wherein the dendritic polymer core is a polyester or a poly(amido-amine).

6. The unimolecular nanoparticle of claim 1, wherein the dendritic polymer core is a hyper-branched polymer or a dendrimer.

7. The unimolecular nanoparticle of claim 1, wherein the dendritic polymer core has from 3 to 7 generations.

8. The unimolecular nanoparticle of claim 1, wherein the dendritic polymer core is a poly(amido-amine) dendrimer having 3 to 4 generations.

9. The unimolecular nanoparticle of claim 1, wherein the dendritic polymer core is a hyperbranched polyester having 3 to 4 generations.

10. The unimolecular nanoparticle of claim 1, wherein the cationic polymer comprises a polyamide backbone, disulfide linkers, amino and/or ammonium salt groups, and imidazole and/or imidazolium salt groups.

11. The unimolecular nanoparticle of claim 10, wherein the cationic polymers comprise
ethylene-disulfide-ethylamino groups and/or salts thereof, and
ethylene-disulfide-ethylaminocarbonylimidazole groups and/or salts thereof.

12. The unimolecular nanoparticle of claim 1, wherein the targeting ligand is a cofactor, carbohydrate, peptide, antibody, nanobody, or aptamer.

13. The unimolecular nanoparticle of claim 1, wherein the targeting ligand is selected from the group consisting of folic acid, mannose, GE11, cRGD, KE108, octreotide, TAT cell penetrating peptide, PSMA aptamer, TRC105, 7D12 nanobody, and CTB.

14. A complex comprising the unimolecular nanoparticle of claim 1 and a therapeutic RNA within the unimolecular nanoparticle.

15. The complex of claim 14, wherein the therapeutic RNA is an siRNA.

16. The complex of claim 14, wherein
the dendritic polymer core is a hyperbranched polyester having 3-4 generations and a molecular weight of about 3,600 to about 7,400 Da;
the pH-sensitive linker is a benzylimine;
each cationic polymer has a polyasparagine backbone attached to:
ethylene-disulfide-ethylamino and/or ethylene-disulfide-ethylammonium salt groups, and
ethylene-disulfide-ethylamidoimidazole and/or ethylene-disulfide-ethylamidoimidazolium salt groups;
wherein the ratio of the amino and/or ammonium salt groups to imidazole and/or imidazolium salt groups is from 1:1 to 5:1.

17. A composition comprising the unimolecular nanoparticle of claim 1 and a pharmaceutically acceptable carrier.

18. A kit comprising a package containing the unimolecular nanoparticle of claim 1, a package containing an effective amount of siRNA, and directions for use of the kit.

19. A siRNA-loaded unimolecular nanoparticle comprising the unimolecular nanoparticle of claim 1 and a siRNA, wherein the loading of siRNA is about 10 wt % to about 20 wt %, based on the total siRNA-loaded unimolecular nanoparticle weight.

20. The unimolecular nanoparticle of claim 1, wherein the cationic functional groups are selected from the group consisting of primary amines, secondary amines, tertiary amines, amidines, guanidines, and combinations of two or more thereof.

21. The unimolecular nanoparticle of claim 1, wherein the weakly basic groups have a pKa of about 5.5 to about 7.0.

22. A method of preparing a complex comprising the unimolecular nanoparticle of claim 1 and a therapeutic RNA, the process comprising dispersing the therapeutic RNA within the unimolecular nanoparticle.

23. A method of treating a cancer by administering an effective amount of the complex of claim 14, wherein the therapeutic RNA inhibits expression of a gene necessary for survival or growth of the cancer.

* * * * *

SEQUENCE LISTING

```
<160> NUMBER OF SEQ ID NOS: 42

<210> SEQ ID NO 1
<211> LENGTH: 12
<212> TYPE: PRT
<213> ORGANISM: Human immunodeficiency virus
```

```
<400> SEQUENCE: 1

Gly Arg Lys Lys Arg Arg Gln Arg Arg Pro Gln
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Leu Ala Leu Lys Leu Ala Leu Lys Ala Leu Lys Ala Ala Leu Lys
1               5                   10                  15

Leu Ala

<210> SEQ ID NO 3
<211> LENGTH: 15
<212> TYPE: PRT
<213> ORGANISM: Drosophila sp.

<400> SEQUENCE: 3

Arg Gln Ile Lys Trp Phe Gln Asn Arg Arg Met Lys Trp Lys Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gln Ile Arg Ile Trp Phe Gln Asn Arg Arg Met Arg Trp Arg Arg
1               5                   10                  15

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ser Ile Pro Pro Glu Val Lys Phe Asn Lys Pro Phe Val Tyr Leu
1               5                   10                  15

Ile

<210> SEQ ID NO 6
<211> LENGTH: 13
<212> TYPE: PRT
<213> ORGANISM: Rana temporaria

<400> SEQUENCE: 6

Phe Val Gln Trp Phe Ser Lys Phe Leu Gly Arg Ile Leu
1               5                   10

<210> SEQ ID NO 7
<211> LENGTH: 10
<212> TYPE: PRT
<213> ORGANISM: Maurus palmatus
```

```
<400> SEQUENCE: 7

Gly Asp Cys Leu Pro His Leu Lys Leu Cys
1               5                   10

<210> SEQ ID NO 8
<211> LENGTH: 18
<212> TYPE: PRT
<213> ORGANISM: Mus sp.

<400> SEQUENCE: 8

Leu Leu Ile Ile Leu Arg Arg Arg Ile Arg Lys Gln Ala His Ala His
1               5                   10                  15

Ser Lys

<210> SEQ ID NO 9
<211> LENGTH: 24
<212> TYPE: PRT
<213> ORGANISM: Homo sapiens

<400> SEQUENCE: 9

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 10
<211> LENGTH: 30
<212> TYPE: PRT
<213> ORGANISM: Unknown
<220> FEATURE:
<223> OTHER INFORMATION: Description of Unknown:
      Neurturin sequence

<400> SEQUENCE: 10

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30

<210> SEQ ID NO 11
<211> LENGTH: 18
<212> TYPE: PRT
<213> ORGANISM: Drosophila sp.

<400> SEQUENCE: 11

Arg Gln Ile Lys Ile Trp Phe Gln Asn Arg Arg Met Lys Trp Lys Lys
1               5                   10                  15

Gly Gly

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30
```

```
<210> SEQ ID NO 13
<211> LENGTH: 11
<212> TYPE: PRT
<213> ORGANISM: Human immunodeficiency virus

<400> SEQUENCE: 13

Tyr Gly Arg Lys Lys Arg Arg Gln Arg Arg Arg
1               5                   10

<210> SEQ ID NO 14
<211> LENGTH: 18
<212> TYPE: PRT
<213> ORGANISM: Unknown
<220> FEATURE:
<223> OTHER INFORMATION: Description of Unknown:
      SynB1 sequence

<400> SEQUENCE: 14

Arg Gly Gly Arg Leu Ser Tyr Ser Arg Arg Arg Phe Ser Thr Ser Thr
1               5                   10                  15

Gly Arg

<210> SEQ ID NO 15
<211> LENGTH: 10
<212> TYPE: PRT
<213> ORGANISM: Unknown
<220> FEATURE:
<223> OTHER INFORMATION: Description of Unknown:
      SynB3 sequence

<400> SEQUENCE: 15

Arg Arg Leu Ser Tyr Ser Arg Arg Arg Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ile Arg Arg Arg Lys Lys Leu Arg Arg Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Gln Arg Arg Thr Ser Lys Leu Met Lys Arg
1               5                   10

<210> SEQ ID NO 18
<211> LENGTH: 15
<212> TYPE: PRT
<213> ORGANISM: Flock house virus

<400> SEQUENCE: 18

Arg Arg Arg Arg Asn Arg Thr Arg Arg Asn Arg Arg Arg Val Arg
1               5                   10                  15
```

```
<210> SEQ ID NO 19
<211> LENGTH: 19
<212> TYPE: PRT
<213> ORGANISM: Brome mosaic virus

<400> SEQUENCE: 19

Lys Met Thr Arg Ala Gln Arg Arg Ala Ala Arg Arg Asn Arg Trp
1               5                   10                  15

Thr Ala Arg

<210> SEQ ID NO 20
<211> LENGTH: 13
<212> TYPE: PRT
<213> ORGANISM: Human T-cell leukemia virus II

<400> SEQUENCE: 20

Thr Arg Arg Gln Arg Thr Arg Arg Ala Arg Arg Asn Arg
1               5                   10

<210> SEQ ID NO 21
<211> LENGTH: 13
<212> TYPE: PRT
<213> ORGANISM: Human immunodeficiency virus

<400> SEQUENCE: 21

Gly Arg Lys Lys Arg Arg Gln Arg Arg Arg Pro Pro Gln
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Arg Arg Arg Arg Arg Arg Arg Arg Arg Pro Pro Gln
1               5                   10

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 24

Lys Leu Ala Leu Lys Leu Ala Leu Lys Leu Ala Leu Ala Leu Lys Leu
1               5                   10                  15

Ala

<210> SEQ ID NO 25
<211> LENGTH: 27
<212> TYPE: PRT
<213> ORGANISM: Homo sapiens

<400> SEQUENCE: 25

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 26
<211> LENGTH: 27
<212> TYPE: PRT
<213> ORGANISM: Unknown
<220> FEATURE:
<223> OTHER INFORMATION: Description of Unknown:
      FBP sequence

<400> SEQUENCE: 26

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 29
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 29

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 31

Arg Arg Arg Arg Arg Arg Arg Arg Arg Arg Arg Arg Arg Arg Arg Arg
1               5                   10                  15

Arg

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 32

Lys Lys Lys Lys Lys Lys Lys Lys Lys Lys Lys Lys Lys Lys Lys Lys
1               5                   10                  15

Lys

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Aminocaproic acid
<220> FEATURE:
<221> NAME/KEY: MOD_RES
<222> LOCATION: (4)..(4)
<223> OTHER INFORMATION: Aminocaproic acid
<220> FEATURE:
<221> NAME/KEY: MOD_RES
<222> LOCATION: (6)..(6)
<223> OTHER INFORMATION: Aminocaproic acid
<220> FEATURE:
<221> NAME/KEY: MOD_RES
<222> LOCATION: (8)..(8)
<223> OTHER INFORMATION: Aminocaproic acid
<220> FEATURE:
<221> NAME/KEY: MOD_RES
<222> LOCATION: (10)..(10)
<223> OTHER INFORMATION: Aminocaproic acid
<220> FEATURE:
<221> NAME/KEY: MOD_RES
<222> LOCATION: (12)..(12)
<223> OTHER INFORMATION: Aminocaproic acid

<400> SEQUENCE: 33

Arg Xaa Arg Xaa Arg Xaa Arg Xaa Arg Xaa Arg Xaa Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (4)..(4)
<223> OTHER INFORMATION: Aminobutyric acid
<220> FEATURE:
<221> NAME/KEY: MOD_RES
<222> LOCATION: (6)..(6)
<223> OTHER INFORMATION: Aminobutyric acid
<220> FEATURE:
<221> NAME/KEY: MOD_RES
<222> LOCATION: (8)..(8)
<223> OTHER INFORMATION: Aminobutyric acid
<220> FEATURE:
<221> NAME/KEY: MOD_RES
<222> LOCATION: (10)..(10)
<223> OTHER INFORMATION: Aminobutyric acid
<220> FEATURE:
<221> NAME/KEY: MOD_RES
<222> LOCATION: (12)..(12)
<223> OTHER INFORMATION: Aminobutyric acid

<400> SEQUENCE: 34

Arg Xaa Arg Xaa Arg Xaa Arg Xaa Arg Xaa Arg Xaa Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Arg Gly Arg Gly Arg Gly Arg Gly Arg Gly Arg Gly Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Met Arg Met Arg Met Arg Met Arg Met Arg Met Arg
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Thr Arg Thr Arg Thr Arg Thr Arg Thr Arg Thr Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Arg Ser Arg Ser Arg Ser Arg Ser Arg Ser Arg
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Arg Arg Arg Arg Arg Arg Arg Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ala Arg Ala Arg Ala Arg Ala Arg Ala Arg Ala Arg
1               5                   10
```

```
<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Arg Arg Arg Arg Arg Arg
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr His Trp Tyr Gly Tyr Thr Pro Gln Asn Val Ile Gly Gly Gly Gly
1               5                   10                  15

Cys
```